United States Patent [19]

Matsuda et al.

[11] Patent Number: 5,039,613
[45] Date of Patent: Aug. 13, 1991

[54] REAGENTS USED IN A METHOD OF CLASSIFYING LEUKOCYTES BY FLOW CYTOMETRY

[75] Inventors: Syouhei Matsuda; Takashi Sakata; Tomoyuki Kuroda, all of Kakogawa, Japan

[73] Assignee: Toa Medical Electronics Co., Ltd., Kobe, Japan

[21] Appl. No.: 91,984

[22] Filed: Sep. 1, 1987

[30] Foreign Application Priority Data

Nov. 27, 1986 [JP] Japan .................................. 61-282698
Nov. 27, 1986 [JP] Japan .................................. 61-282699

[51] Int. Cl.$^5$ ................................................. G01N 1/30
[52] U.S. Cl. ........................................ 436/17; 436/166; 436/172; 436/174; 436/800; 252/301.16; 252/301.19
[58] Field of Search ................... 436/17, 63, 166, 172, 436/174, 800; 252/301.16, 301.19, 301.21; 8/638, 644

[56] References Cited

U.S. PATENT DOCUMENTS

| | | | |
|---|---|---|---|
| 3,684,377 | 8/1972 | Adams et al. ........................ | 356/36 |
| 3,883,247 | 5/1975 | Adams .................................. | 356/39 |
| 3,916,197 | 10/1975 | Fulwyler ............................. | 250/361 |
| 3,916,205 | 10/1975 | Kleinerman . | |
| 4,066,395 | 1/1978 | Soiron et al. ...................... | 8/657 X |
| 4,073,739 | 2/1978 | Peters ............................... | 252/62.1 P |
| 4,252,534 | 2/1981 | Abel et al. ......................... | 8/654 X |
| 4,400,370 | 8/1983 | Kass .................................... | 424/3 |
| 4,528,256 | 7/1985 | Lind ..................................... | 430/83 |
| 4,581,223 | 4/1986 | Kass . | |
| 4,666,812 | 5/1987 | Wiedemann et al. ............ | 430/77 X |
| 4,751,179 | 6/1989 | Ledis et al. ......................... | 435/34 |
| 4,751,188 | 6/1988 | Valet ................................... | 436/63 |
| 4,760,006 | 7/1988 | Pawlowski ........................... | 430/78 |

FOREIGN PATENT DOCUMENTS

55-18860 5/1980 Japan .
1560729 2/1980 United Kingdom .

OTHER PUBLICATIONS

"Colour Index", vol. 4, London, Society of Dyers and Colourists, 1971, pp. 4417, 4437, 4439, & 4459.
Steinkamp, "Flow Cytometry", Review of Scientific Instruments, 55, 1375–1400, (1984).
Kamentsky, "Objective Measures of Information from Blood Cells", Blood Cells 6, 121–140 (1980).
Groner and Tycko, "Characterizing Blood Cells by Biophysical Measurements in Flow," 6 *Blood Cells*, pp. 141–157 (1980).
Shapiro, Schildkraut, Curbelo, Laird, Turner and Hirschfeld, "Combined Blood Cell Counting and Classification with Fluorochrome Stains and Flow Instrumentation," 24 *The Journal of Histochemistry and Cytochemistry*, pp. 396–411 (1976).
Shapiro, "Fluorescent Dyes for Differential Counts by Flow Cytometry: Does Histochemistry Tell Us Much More than Cell Geometry?," *The Journal of Histochemistry and Cytochemistry*, pp. 976–989 (1977).

*Primary Examiner*—David L. Lacey
*Assistant Examiner*—Jeffrey R. Snay
*Attorney, Agent, or Firm*—Fitch, Even, Tabin & Flannery

[57] ABSTRACT

Three methods for classifying leukocytes with a flow cytometer by optical measurements on fluorochrome-stained blood cells or those which have been so treated as to provide varying intensity in forward scattered light are useful in the practice of clinical testing. Also included are reagents employed in the practice of such methods.

2 Claims, 34 Drawing Sheets

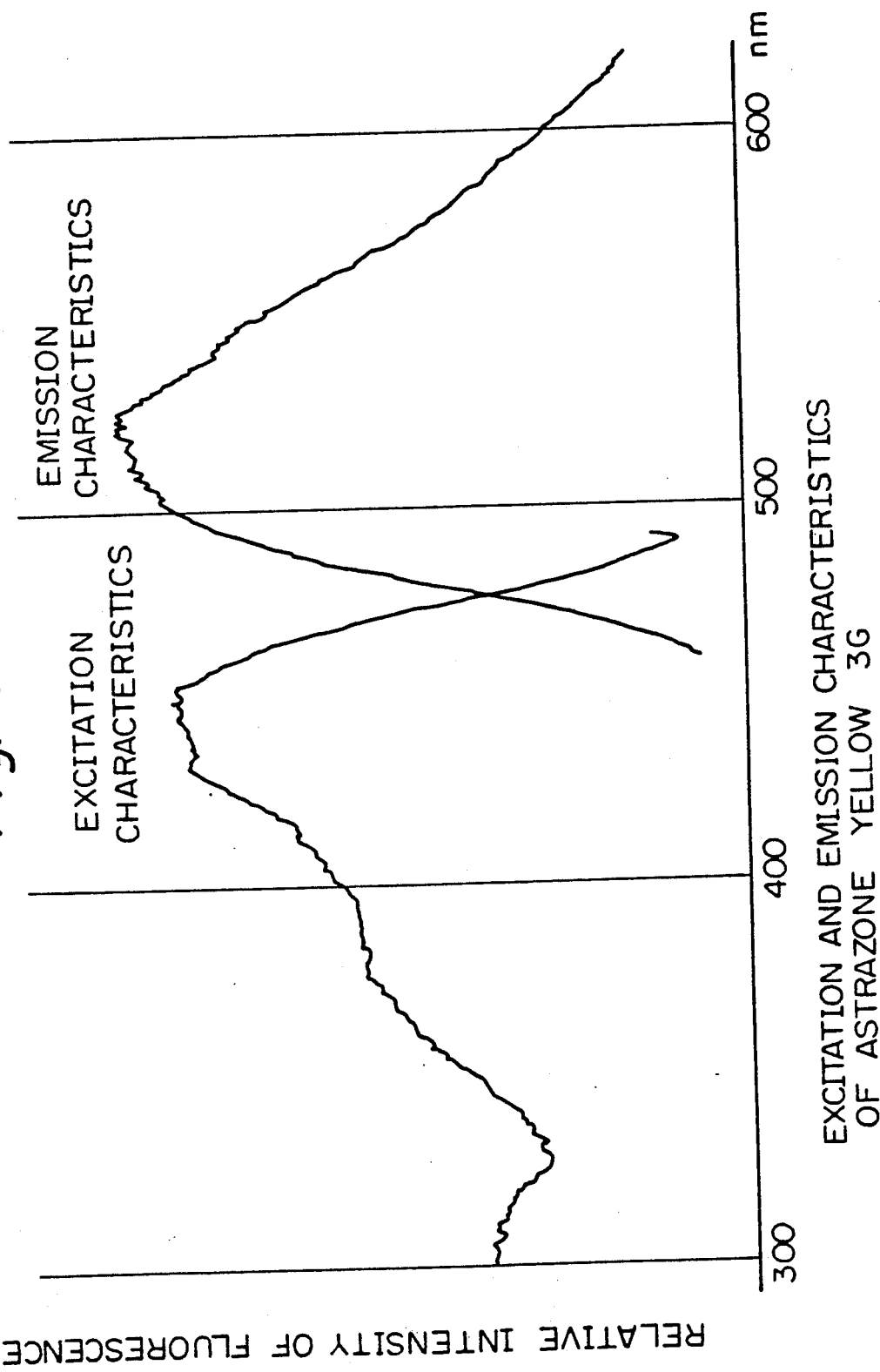

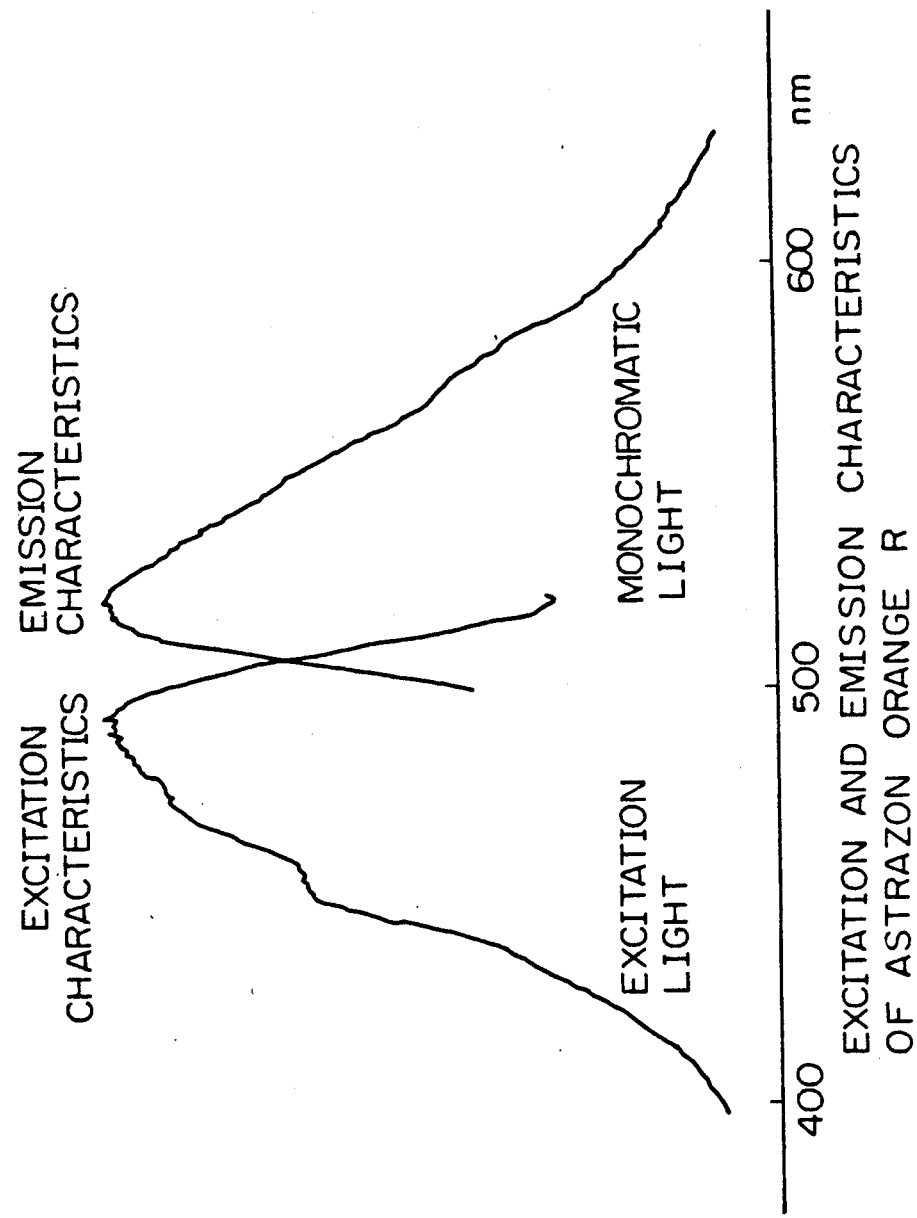

pH DEPENDANCY OF RATIO OF RELATIVE AVERAGE FLUORESCENCE INTENSITY OF EOSINOPHILS TO THAT OF NEUTROPHILS pH DEPENDANCY OF RATIO OF RELATIVE AVERAGE FLUORESCENCE INTENSITY OF EOSINOPHILS TO THAT OF NEUTROPHILS

Fig. 23
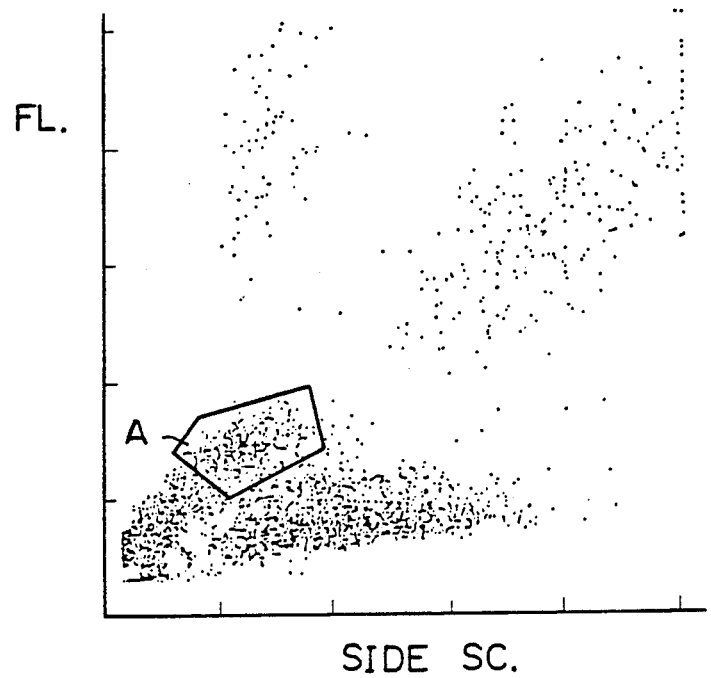
Fig. 24 1ppm
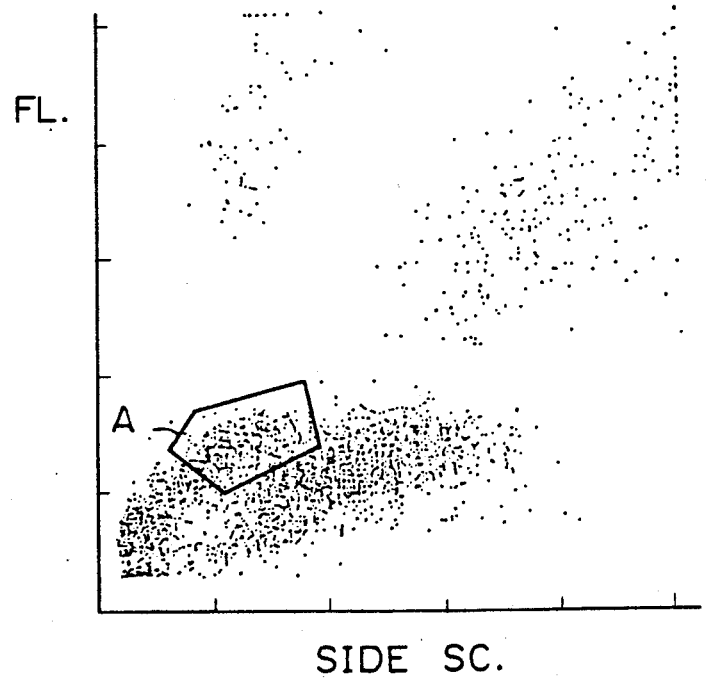

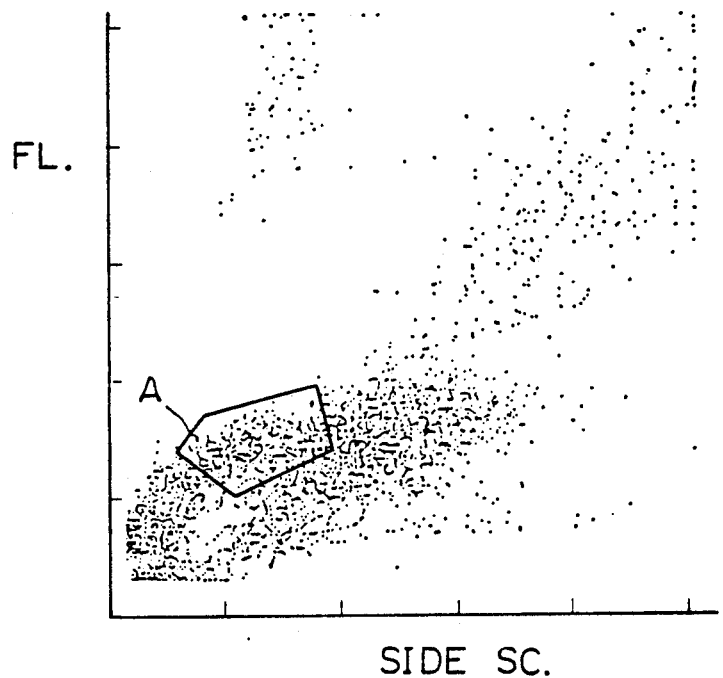
Fig. 25  2ppm
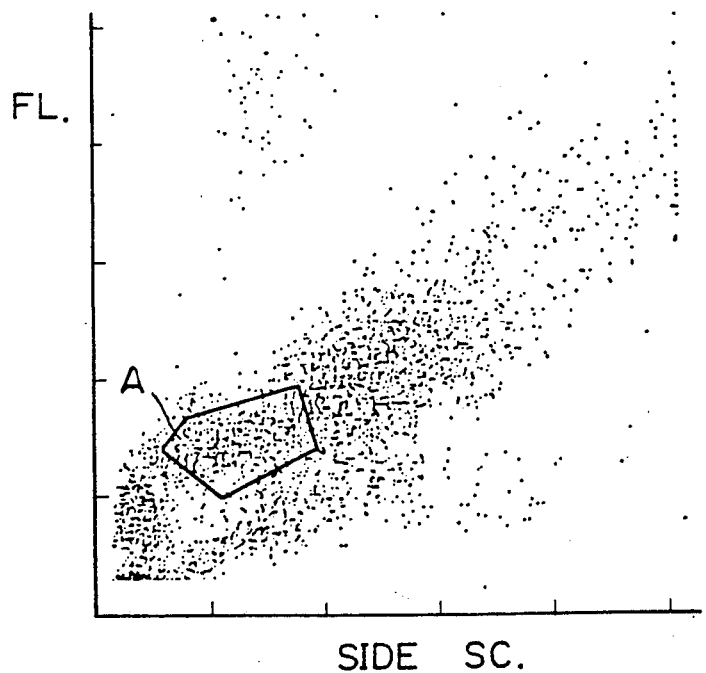
Fig. 26  5ppm

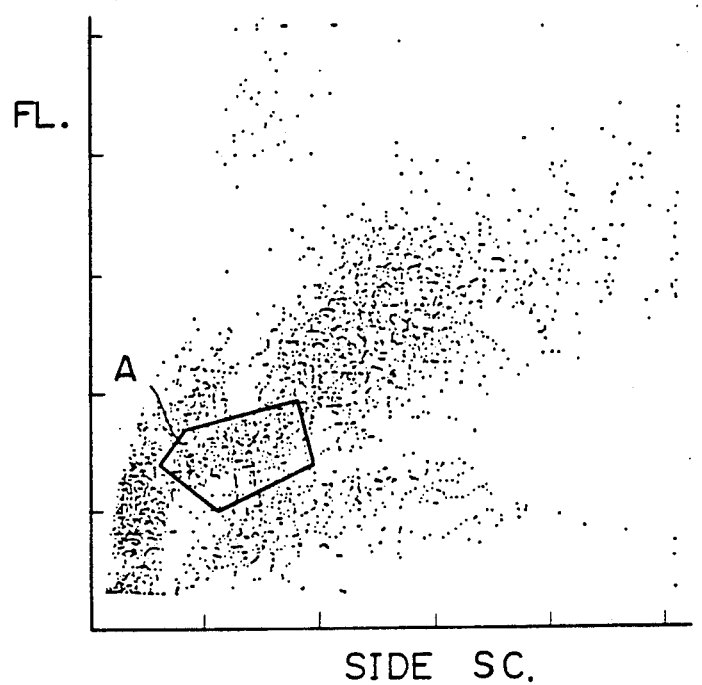
Fig. 27  10 ppm
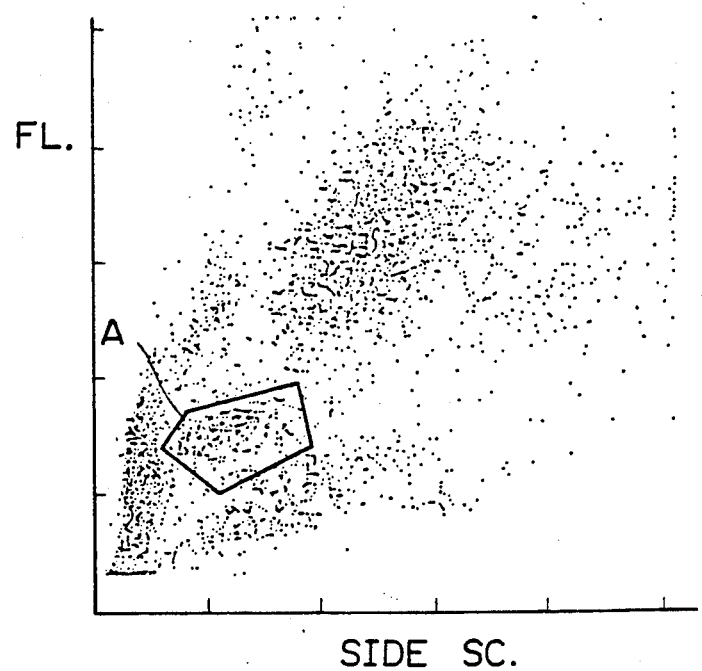
Fig. 28  20 ppm

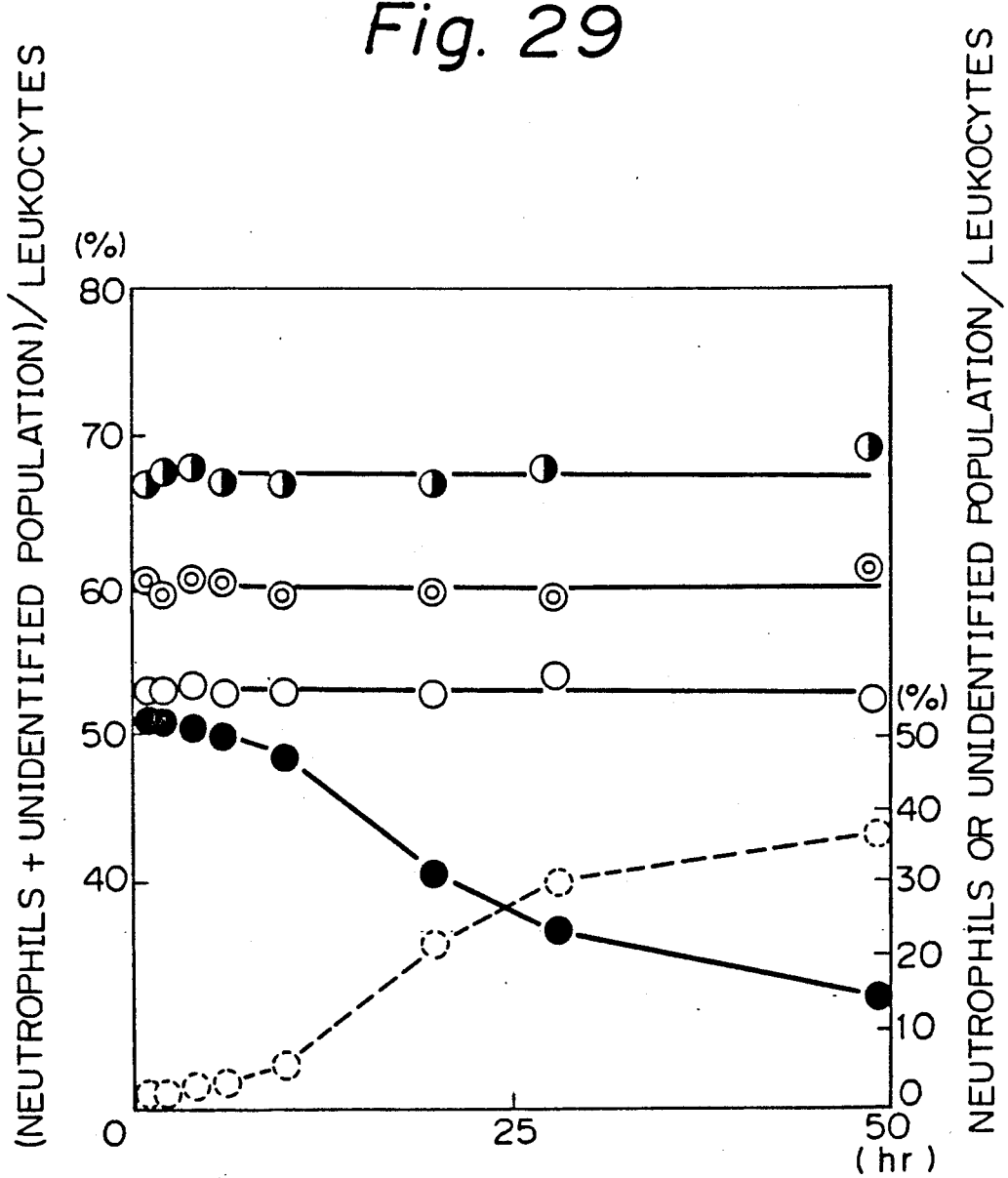

REAGENTS USED IN A METHOD OF CLASSIFYING LEUKOCYTES BY FLOW CYTOMETRY

FIELD OF THE INVENTION

The present invention relates to methods for classifying leukocytes in the practice of clinical testing, and reagents used in that method. More particularly, the present invention relates to three methods for classifying leukocytes with a flow cytometer by means of optical measurements on fluorochrome-stained blood cells or those which have been so treated as to provide varying intensity in forward scattered light. The present invention also relates to reagents employed in the practice of such methods.

BACKGROUND OF THE INVENTION

Leukocytes in the peripheral blood of normal subjects can be classified as being of five types consisting of lymphocytes, monocytes, neutrophils, eosinophils, and basophils. Different leukocyte types have different functions and counting of leukocytes in the blood according to their type will provide valuable information for diagnostic purposes. For instance, an increase in the number of neutrophils is associated with such diseases as inflammations, myocardial infarction and leukemia, and a decrease in their number is associated with viral diseases, hypoplastic anemia, agranulocytosis, etc. On the other hand, an increase in the number of eosinophils is found in such diseases as parasitosis, Hodgkin's disease and allergosis. An increased number of monocytes occurs either during the convalescence period of patients suffering from infectious diseases or in such diseases as monocytic leukemia.

Classification and counting of leukocytes have been made most commonly by the differential counting method which is also referred to as the visual counting method or simply as the manual method. In this method, a blood sample is smeared on a glass slide and the blood corpuscles in the smear are fixed and stained for examination by microscopy. The technician identifies the type of individual leukocytes according to their morphological features (e.g., their size, the morphology of their nucleus and cytoplasm, and the presence or absence of granules) or the degree of dye uptake and performs classification and counting of them. At ordinary laboratories, 100-200 leukocytes are usually counted for each sample and the percentage of the total leukocyte count occupied by each type of corpuscle is recorded as a measured value.

The differential counting method has several disadvantages. First, microscopic observation must be preceded by cumbersome procedures for preparing a specimen that involve such steps as smearing a blood sample on a glass slide, fixing the corpuscles and staining them. Secondly, it is a great burden for the technician to identify subtle differences between corpuscles by microscopic classification and counting. Thirdly, it is difficult even for a skilled technician to yield consistent counts by the manual method since aside from the small number of leukocytes computed, the smeared sample often has an uneven distribution of blood corpuscles.

Various methods have been proposed for eliminating these disadvantages of the manual method of leukocyte classification by achieving automation and such automated techniques may be roughly divided into two types. The first method consists of recording the images of corpuscles with a video camera or some other suitable imaging device and classifying the leukocytes by means of image processing on a computer. The operating principle of this method is similar to that of the conventional visual counting method but primarily due to the existence of many corpuscles that defy classification by processing with a computer, this method has not yet become an ideal alternative to the manual method. Furthermore, this method is not economically feasible since it requires sophisticated equipment which is large and costly.

The other approach toward automatic classification and counting of leukocytes is based on a flow system. In this method, a blood sample having corpuscles suspended in a diluent is permitted to flow in such a way that the corpuscles will individually (one by one) pass through a constricted detector, and leukocyte classification is made by analyzing the signal generated by the detector. This second method of leukocyte counting which makes use of a flow system is further subdivided into two categories.

In a method of the first category, an electrolyte in which all red cells that were present have been destroyed with a lysing agent so that only leukocytes will be suspended is permitted to flow through an orifice, and the change in electrical impedance that occurs at the orifice when each corpuscle passes through it is detected, with the magnitude of the detected signal being used as a basis for classification of leukocytes.

A method of the second category is characterized by the use of a flow cytometer that comprises a light source, a flow cell that permits the blood cells in a sample to flow one by one through a constricted channel, a photometric unit that detects light issuing from each blood cell, and an analyzer for analyzing the detected signal. In this method, the corpuscles in the sample which are stained are illuminated under light and the fluorescence emitted from the irradiated corpuscles is detected, optionally together with scattered light, with leukocyte classification being made in accordance with the intensity of the detected signal.

Techniques that fall within the category of this flow cytometric method are described in, for example, Japanese Patent Publication No. 853/1984 and L. A. Kamentsky, Blood, 6, 121-140 (1980). According to these techniques, a blood sample is stained with 10 volumes of an acridine orange solution, incubated for 1 minute, and irradiated under a light source such as an argon ion laser. The green fluorescence and red fluorescence that are emitted from the individual corpuscles are measured and classification and counting of leukocytes are subsequently made based on a two-dimensional plot of the fluorescence measurements.

Other examples of techniques that are classified as being within the flow cytometric approach are shown in Unexamined Published Japanese Patent Application No. 20820/1975, H. M. Shapiro et al., J. Histochem. Cytochem., 24 (1) 396-411 (1976); and supra, 25 (8) 976-989 (1977). According to these methods, a blood sample is stained with 4 volumes of a Dye Solution I, incubated for 3 minutes, further mixed with 20% formaldehyde in a volume equal to the blood, fixed for 5 minutes, and diluted with a diluting Dye Solution II to obtain a concentration 15-20 times as low as the initial value. The so prepared specimen is subjected to measurement with a flow cytometer.

The flow cytometer employed in the these methods uses either a mercury lamp that produces three different wavelengths of light or three lasers, so as to excite the three fluorescent stains in each of the dye solutions. The parameters measured are three kinds of fluorescence, forward scattered light, 90~C scattered light and absorbed light. Based on these six parameters, two-dimensional plots are constructed in four stages and analyzed to make leukocyte classification and counting.

Japanese Patent Application No. 213715/1986, filed on Sept. 10, 1986, discloses a one-step staining process consisting of staining a blood sample with a dye solution comprised of a buffer solution, inorganic salts and fluorescent stains. But this method has the problem that unlyzed erythrocytes may adversely affect measurement data to produce unreliable results.

In the first version of the method that uses a flow system for leukocyte classification and counting, the disruption of erythrocytes is a prerequisite but depending on a blood sample, it is impossible to effect complete lysis of erythrocytes and the accuracy of measurements may be impaired in such a case.

The examples of the flow cytometric approach that are described in Japanese Patent Publication No. 853/1984 and Blood Cells, 6, 121-140 (1980) are characterized by performing measurements before dye absorption by the cells reaches an equilibrium, or at the time when the difference between the intensities of fluorescence from individual leukocytes attains a maximum during the staining process. However, the time required for attaining an appropriate level of fluorescence intensity in a sample whose leukocyte count is at either one of two extremes will be different from the time for a normal sample, and an appropriate staining time must be selected for each sample. As a further problem, this method relies solely on the differential intensity of fluorescence for leukocyte classification and does not necessarily ensure precise separation between different leukocyte types such as lymphocytes and monocytes.

The other examples of the cytometric approach that are described in Unexamined Published Japanese Patent Application No. 20820/1975, J. Histochem, Cytochem., 24 (1) 396-411 (1976) and supra, 25 (8) 976-989 (1977) have the disadvantage that they involve many steps of operation, take a prolonged staining time and require the use of reagents in a complex system. Furthermore, practice of these methods requires a very sophisticated and costly apparatus that includes three light sources and which is capable of measuring six parameters. In addition, analysis of such a large number of parameters is inevitably complicated and requires an analyzer of large capacity.

All of the prior art techniques of flow cytometric approach, including the method proposed by Japanese Patent Application No. 213715/1986 have one common problem in that detection with a flow cytometer is impossible if neutrophils in a blood sample become dead when a long time has passed before measurement. In order to avoid this problem, measurements by these flow cytometric methods always require the use of fresh blood samples.

The present invention has been accomplished in order to solve the aforementioned problems of the prior art techniques for leukocyte classification and counting and it provides reagents and three methods that enable accurate classification and counting of leukocytes by simple procedures.

SUMMARY OF THE INVENTION

The present invention provides three different methods for classification and counting of leukocytes, namely, a one-step and a two-step method, each of which is based on the measurement of two signals, one being a fluorescence signal and the other being a right-angle (or rectangular) scattered light signal, and a method that is based on the measurement of a forward scattered light signal and a right-angle (or rectangular) scattered light signal (the last-mentioned method is hereinafter referred to as a third method).

The one-step method comprises the following steps (a) to (c):

(a) a step of preparing a specimen for measurement by adding a sample of anti-coagulated blood to a dye solution composed of a fluorochrome dye for selective staining of eosinophils and basophils, a fluorochrome dye for staining the nuclei of leukocytes, a buffer for maintaining a pH of 6.0–11.0, and an osmolarity compensating agent for adjusting the osmolarity of the dye solution to a value at which the leukocytes remain unchanged in shape, and of allowing the blood sample to be stained until an equilibrium is reached;

(b) a step of permitting the prepared specimen for measurement to flow through a flow cytometer, differentiating leukocytes from all other corpuscles by intensity of fluorescence, and measuring the signals of right-angle (rectangular) scattered light and of fluorescence from leukocytes; and (c) a step of identifying the type of each of the leukocytes based on the right-angle scattered light and fluorescence signals emitted therefrom, counting the number of detected leukocytes according to their type, and calculating the proportions of individual leukocyte types.

The two-step method comprises the following steps (a) to (d):

(a) a step of lysing the erythrocytes in a sample of anti-coagulated blood by adding it to a hypotonic first fluid composed of a fluorochrome dye for selective staining of eosinophils and basophils, a fluorochrome dye for staining the nuclei of leukocytes, and a buffer for maintaining an acidic pH range;

(b) a step of staining the leukocytes in the so-treated blood sample by adding to it a second fluid that is composed of a buffer for neutralizing the acid in the buffer in the first fluid and maintaining a pH suitable for staining, and an osmolarity compensating agent for adjusting the osmolarity of the resulting fluid to a value at which the leukocytes remain unchanged in shape;

(c) a step of permitting the stained sample to flow through a flow cytometer, differentiating leukocytes from all other corpuscles and ghosts by intensity of fluorescence, and measuring the signals of fluorescence and right-angle (rectangular) scattered light from leukocytes; and (d) a step of identifying the type of each of the leukocytes based on the fluorescence and right-angle scattered light signals emitted therefrom, counting the number of detected leukocytes according to their type, and calculating the proportions of individual leukocyte types.

The third method of the present invention comprises the following steps (a') to (d'):

(a') a step of lysing the erythrocytes in a sample of anti-coagulated blood by adding it to a hypotonic first fluid composed of a material that selectively decreases the intensity of forward scattered light from eosinophils and basophils, and a buffer for maintaining an acidic pH range;

(b') a step of initiating a leukocyte reaction by adding to the lysed blood sample a second fluid that is composed of a buffer for neutralizing the acid in the buffer in the first fluid and maintaining a pH suitable for leukocyte reaction, and an osmolarity compensating agent for adjusting the osmolarity of the resulting reaction solution to a value at which the leukocytes remain unchanged in shape;

(c') a step of permitting the sample of flow through a flow cytometer and measuring the signals of forward scattered light and right-angle scattered light from leukocytes; and (d') a step of identifying the type of each of the leukocytes based on the forward scattered light and right-angle scattered light signals emitted therefrom, counting the number of detected leukocytes according to their type, and calculating the proportions of individual leukocyte types.

In this third method, a fluorochrome dye for staining the nuclei of leukocytes may be incorporated in the first fluid and step (c') may include the operation of identifying different types of leukocytes by intensity of fluorescence signal in order to extract forward scattered light and right-angle scattered light signals solely from the leukocytes.

The reagent system for use in the classification of leukocytes into five types by flow cytometry in accordance with the present invention is composed of:

(1) a fluorochrome dye that selectively stains eosinophils and basophils or a substance that reduces forward scattered light, an example of such fluorochrome or substance being Astrazon Yellow 3G; and (2) one of the following fluorochrome dyes that stain the nuclei of leukocytes (this is necessary in both the one-step and two-step methods but may be omitted in the third method):

Acridine Red;
Rhodamine S;
Rhodamine 6G;
Rhodamine B;
Rhodamine 19 perchlorate;
Rhodamine 123;
Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1'-diethyl-9-methylthiocarbocyanine bromide;
2-[γ-1'-ethil-4',5'-benzothiazolylidene)propenyl]-1-ethyl-4,5-benzoxazolium iodide;
Astrazon Red 6B;
C.I. Basic Violet 16;
2-(p-dimethylaminostyryl)-1-ethyl-4,5-benzothiazolium iodide;
2,4-bis(p-dimethylaminostyryl)-1-ethyl-pyridnium iodide;
2,6-bis(p-dimethylaminostyryl)-1-ethyl-pyridnium iodide;
TA-2 (Nippon Kankoh-Shikiso Kenkyusho Co., Ltd., Okayama, Japan); and
Astrazon Orange R.

The last-mentioned Astrazon Orange R is particularly preferred for use as component (2).

BRIEF DESCRIPTION OF THE DRAWINGS

FIG. 5 is a graph showing the excitation and fluorescence characteristics of Astrazon Yellow 3G;

FIG. 8 is a graph showing the excitation and fluorescence characteristics of Astrozon Orange R;

FIGS. 23 to 28 are two-dimensional plots of the intensities of fluorescence and right-angle scattered light for samples containing varying amounts of FDA;

FIG. 29 is a graph showing the changes in the percentage of neutrophils plus cells in an unidentified population and in the percentages of neutrophils and cells in the unidentified population as a function of the period of time for which samples were left to stand;

Figure 30:
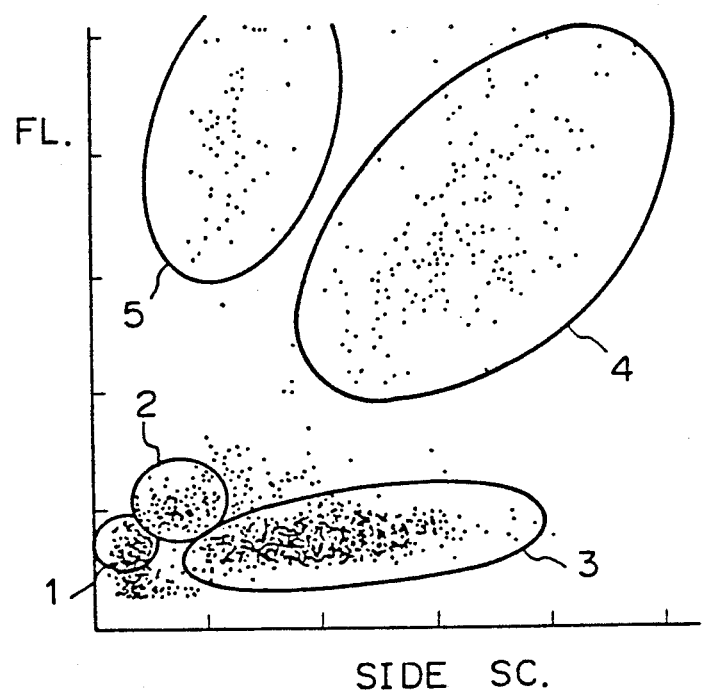
FIG. 30(a) is a two-dimensional plot of the intensities of fluorescence and right-angle scattered light as measured to classify leukocytes.
FIG. 30(b) is a two-dimensional plot of the intensities of forward scattered light and right-angle scattered light as measured to classify leukocytes.
Figure 30:
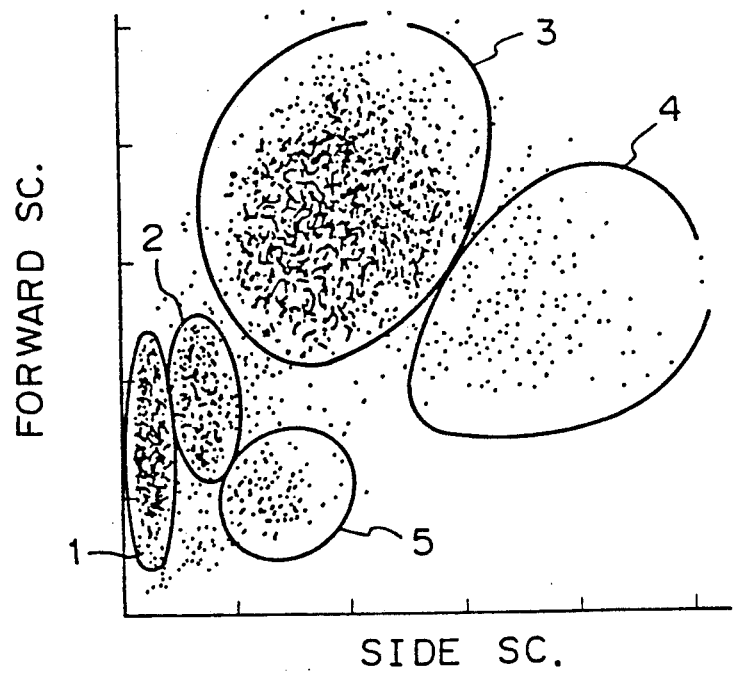

In accordance with the present invention not only a forward and a right-angle scattering light signal but also a fluorescence signal is produced from leukocytes. The fluorescence signal reflects the cytochemical characters of leukocytes and depending on the interaction between stains and individual leukocyte types, signals of different intensities are produced from the leukocytes. The right-angle scattering light signal reflects the structural information of an individual white cell. The larger the nucleus of a white blood cell and the more granules that are present in it, the greater light reflection will occur in the cell to produce more intense right-angle scattered light. A lymphocyte contains very few or no granules, so the scattered light produced from the lymphocyte is the weakest of all leukocytes. On the other hand, a neutrophil contains many granules and has a large nucleus, so that it produces the most intense scattered light. Monocytes, eosinophils and basophils produce scattered light the intensity of which is intermediate between the intensities of scattered light from lymphocytes and neutrophils. The forward scattered light provides information about the internal state and size of blood cells, and in the third method of the present invention, the forward scattered light from eosinophils and basophils is attenuated so that it can be adapted to classification of leukocytes into five types. The relative intensities of fluorescence and right-angle scattered light from individual leukocytes are plotted in FIG. 30(a), and the relative intensities of forward scattered light and right-angle scattered light from the leukocytes are plotted in FIG. 30(b).

Of the three kinds of light produced from leukocytes, fluorescence is the weakest and requires a highly sensitive photomultiplier tube for its measurement, which adds to the overall cost of the equipment.

The right-angle scattered light is more intense than fluorescence and may be measured with a photomultiplier tube of relatively low sensitivity. The forward scattered light is very intense as compared with fluorescence and right-angle scattered light, so it does not require any light-receiving device of high sensitivity such as a photomultiplier tube; instead, it can be measured with a photodiode after being converged with a condenser lens.

Therefore, as will be described below in detail, by combining a forward scattered light signal either with a fluorescence signal or with a right-angle scattered light signal, leukocytes can be classified into five types with a simple and less costly apparatus.

In the one-step or two-step method of the present invention, no cumbersome operations involving a complicated preliminary treatment are required and only the leukocytes in blood can be classified and counted with a flow cytometer after a simple one- or two-step staining or reaction operation has been completed.

Figure 1A:
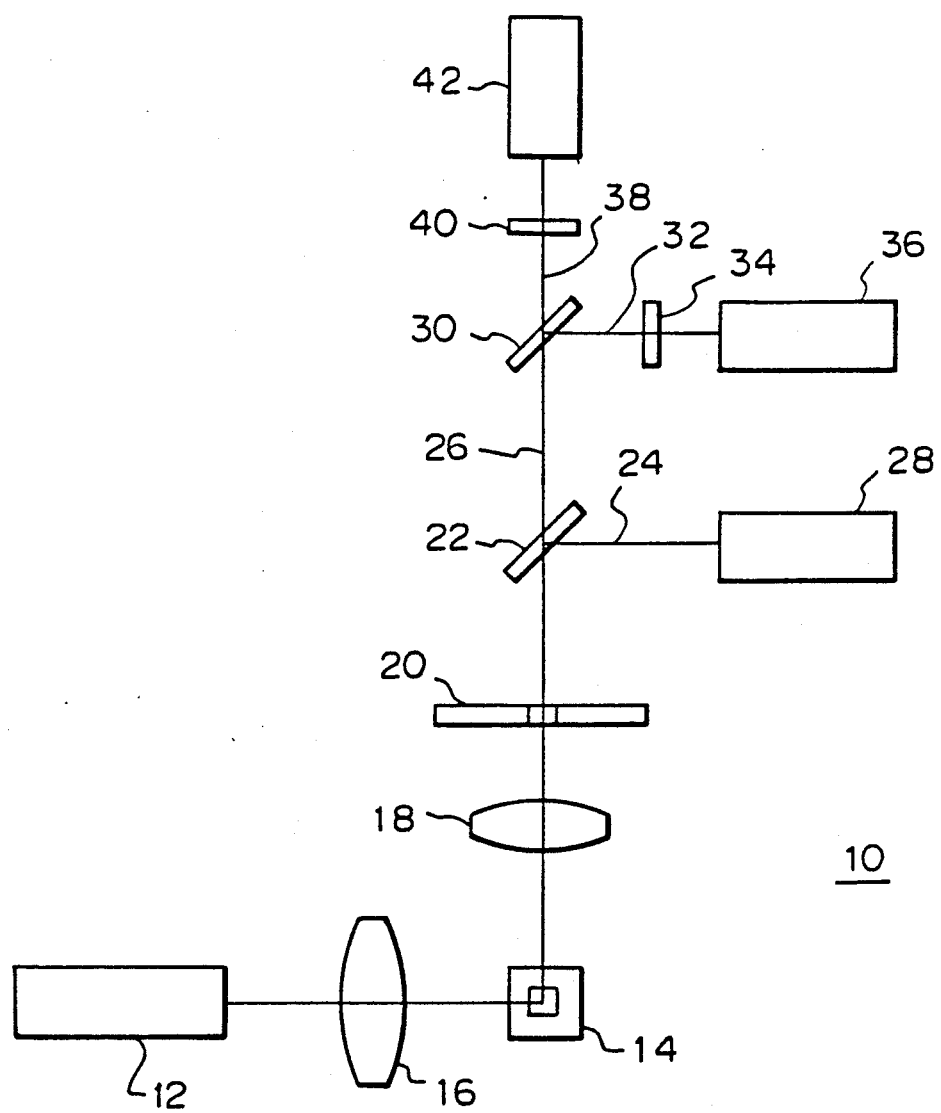
FIG. 1(a) is a schematic diagram of the optics of a flow cytometer that may be employed in implementing the one-step or two-step method of the present invention.

A specific example of the optics of a flow cytometer employed in the present invention is hereunder described with reference to FIGS. 1(a) and 1(b). The optics shown in FIG. 1(a) is used in a flow cytometer designed for measuring right-angle scattered light, red fluorescence and green fluorescence. The optics, generally indicated by 10, uses an argon ion laser 12 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated by the laser light, they produce scattered light and fluorescence. The right-angle scattered light and the fluorescence are converged with a condenser lens 18 and pass through an aperture 20 to fall upon a dichroic mirror 22. The dichroic mirror 22 reflects the right-angle scattered light 24 and transmits the fluorescence 26. The right-angle scattered light 24 reflected from the dichroic mirror 22 is detected in a photomultiplier tube 28. Of the two kinds of fluorescence 26 that pass through the dichroic mirror 22, red fluorescence 32 is reflected by a dichroic mirror 30 and green fluorescence 38 is transmitted through that mirror. The reflected red fluorescence 32 passes through a color filter 34 and is detected in a photomultiplier tube 36. The transmitted green fluorescence 38 passes through a color filter 40 and is detected in a photomultiplier tube 42.

Figure 1B:
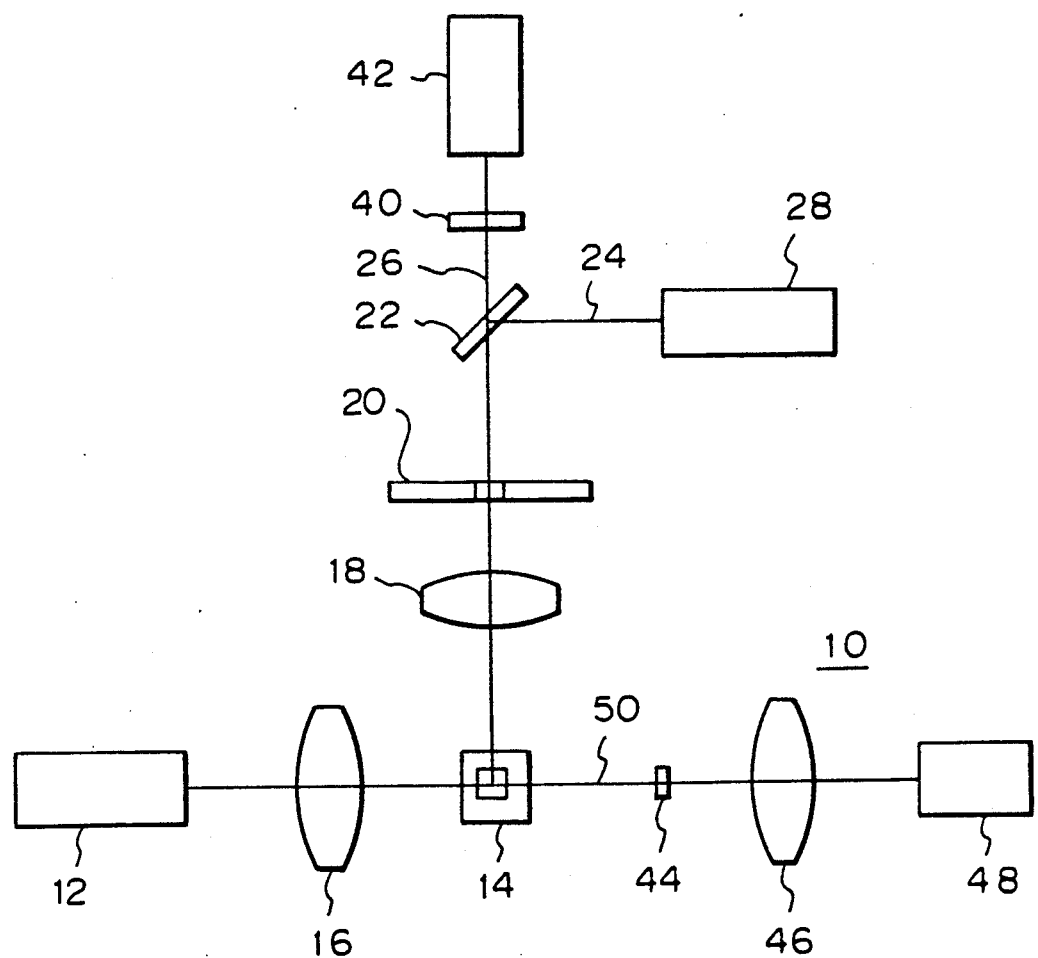
FIG. 1(b) is a schematic diagram of the optics of a flow cytometer that may be employed in implementing the third method of the present invention.
Figure 2:
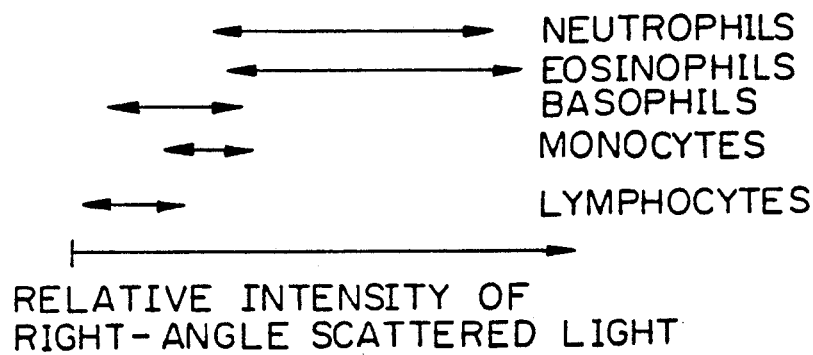
FIG. 2 is a graph showing the relative intensities of right-angle scattered light from five different types of leukocytes.

The optics shown in FIG. 1(b) is used in a flow cytometer designed for measuring forward scattered light, right-angle scattered light, and fluorescence. As will be shown later in Example 3, fluorescence is necessary in the third method of the present invention if leukocytes are to be distinguished from all other corpuscles by a fluorescence signal. Fluorescence is not necessary if the two groups of corpuscles are distinguished from each other by forward scattered light. In Example 3, fluorescence measurement was necessary because it involved a comparison with a method of leukocyte classification based on the intensity of fluorescence. In Example 3, fluorescence was also used as a means for distinguishing leukocytes from other corpuscles. As in the case shown in FIG. 1(a), the optics generally indicated by 10 uses an argon ion laser 12 as a light source and it operates at a wavelength of 488 nm, producing an output of 10 mW. Light emitted from the laser 12 is converged by a cylindrical lens 16 and illuminates a blood sample flowing through a flow cell 14.

When the stained leukocytes in the sample are irradiated with the laser light, they produce scattered light and fluorescence. The right-angle scattered light and the fluorescence are converged with a condenser lens 18 and pass through an aperture 20 to fall upon a dichroic mirror 22. The dichroic mirror 22 reflects the right-angle scattered light 24 and transmits the fluorescence 26. The right-angle scattered light 24 reflected from the dichroic mirror 22 is detected in a photomultiplier tube 28. The fluorescence 26 that has been transmitted through the dichroic mirror 22 passes through a color filter 40 and is detected by a photomultiplier 42.

The remaining component of light from the light source 12 is simply transmitted through the flow cell 14 in the forward direction and the resulting forward scattered light 50 is blocked by a beam stopper 44 so that it will not directly encounter a photodiode 48. Light that passes through the beam stopper 44 is converged with a condenser lens 46 and is subsequently received by the photodiode 48.

The color filter 40, photomultiplier tube 42 and dichroic mirror 22 are employed to perform fluorescence measurement for the purpose of providing a reference for comparison between the results of measurement with forward scattered light and right-angle scattered light and those of measurement with fluorescence and right-angle scattered light. The dichroic mirror 22 is positioned to separate fluorescence from right-angle scattered light so that the former can be measured as a reference. If it is necessary to measure only the right-angle scattered light, the photomultiplier tube 28 may be positioned immediately after the aperture 20. If fluorescence is not measured as a reference, the color filter 40, dichroic mirror 22 and the photomultiplier tube 42 which require high sensitivity of measurement can be entirely eliminated and the resulting equipment will be very simple in construction and can be fabricated at low cost.

Figure 3:
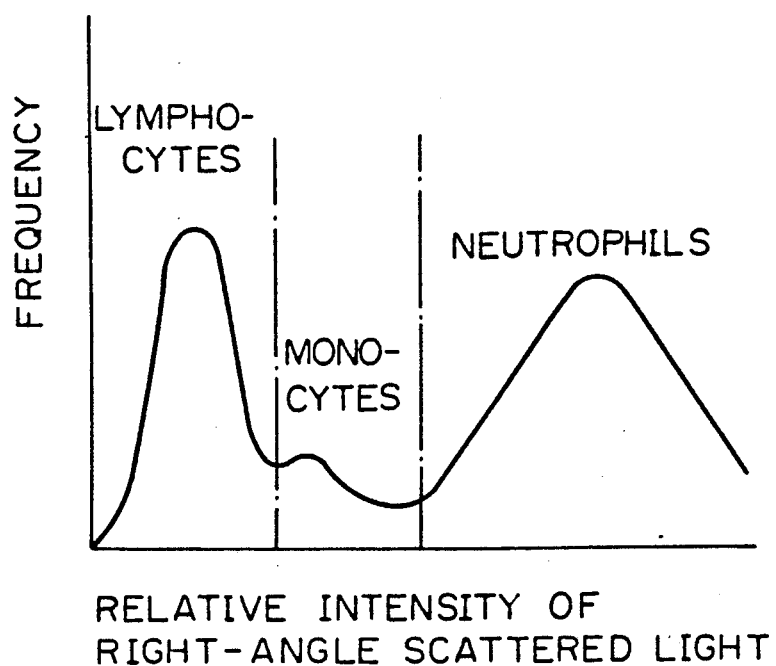
FIG. 3 is a frequency distribution curve for the relative intensities of right-angle scattered light from lymphocytes, monocytes and neutrophils as influenced by the coincidence of erythrocytes and leukocytes.

In the one-step method, erythrocytes in the blood sample emit only fluorescence of very low intensity, so if all that is needed is to measure the intensity of fluorescence, erythrocytes will not interfere with the counting of leukocytes even if coincidence of erythrocytes and leukocytes occurs (i.e., erythrocytes and leukocytes pass through the detecting portion simultaneously). However, if one wants to measure the scattered light, erythrocytes which produce scattered light having an intensity comparable to that of the scattered light emitted from leukocytes will interfere with the counting of leukocytes. In this case, one may measure fluorescence and scattered light simultaneously and regard as leukocytes only the corpuscles that emit fluorescence having an intensity greater than a certain level. However, if coincidence of leukocytes and erythrocytes occurs, the scattered light from erythrocytes is superposed on the scattered light from leukocytes, thereby making accurate measurement of scattered light from the leukocytes impossible. In the optics 10 of a flow cytometer shown in FIG. 1(a), a blood sample is permitted to flow through the flow cell 14 after it has been diluted by, for example, 20 folds, so that the probability of coincidence of erythrocytes and leukocytes is reduced and the potential interference by erythrocytes is decreased to a level that can be disregarded for practical purposes. However, if, as in the two-step method, eosinophils and basophils are excluded by measurement of the intensity of fluorescence and if the intensities of right-angle scattered light from the remaining three types of leukocytes, i.e., lymphocytes, monocytes and neutrophils, are plotted, the populations of the three leukocyte types cannot be completely separated from one another as shown in FIG. 3.

Figure 4:
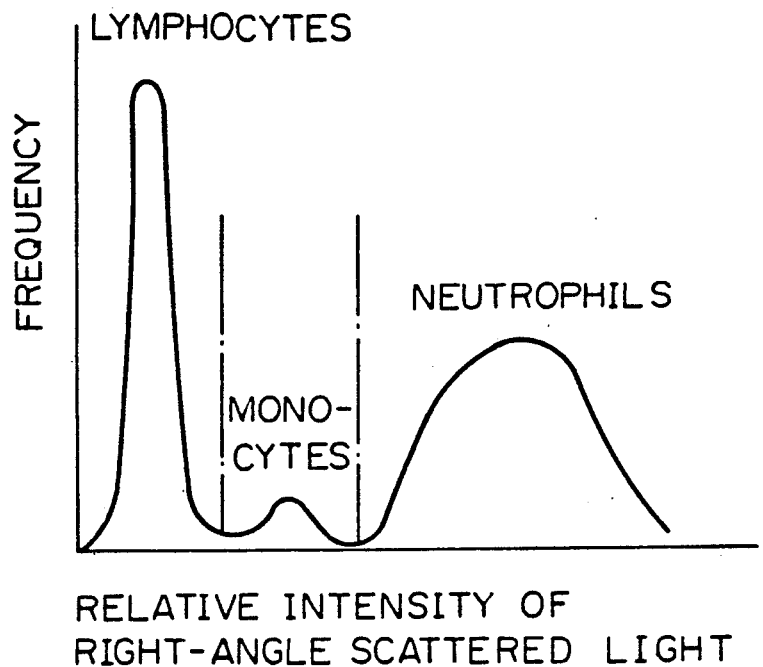
FIG. 4 is a frequency distribution curve for the relative intensities of right-angle scattered light from lymphocytes, monocytes and neutrophils in the absence of any coincidence of erythrocytes and leukocytes.

If the sample is further diluted so that the probability of coincidence of erythrocytes and leukocytes is reduced to such a level that the potential interference by erythrocytes can be completely disregarded, the populations of lymphocytes, monocytes and neutrophils can be completely separated from one another as shown in FIG. 4, which is a plot of the intensities of right-angle scattered light from these three types of leukocytes. However, in order to ensure the desired precision of measurement, at least about 10,000 leukocytes must be counted. Therefore, the practical value of diluting the blood sample is limited by the prolonged time required for completion of measurement.

The aforementioned problems associated with the interference by erythrocytes can be solved if they are eliminated from the blood sample by a suitable technique, such as lysing, but this idea has not been put to practice in the present art because of the absence of any erythrocyte-eliminating method, such as lysing, that matches the conditions of staining. There is no prior art technique that performs lysing of erythrocytes in preparation for the classification of leukocytes into five types by staining with fluorochrome dyes. Also, there is no technique available that successfully lyses only erythrocytes within one minute and which yet does not deteriorate the right-angle scattered light (morphological information) from leukocytes.

Blood samples for leukocyte counting that are free from erythrocytes are commonly prepared by the following methods:
i) lysing of erythrocytes
  a) treatment with a surfactant;
  b) treatment with an ammonium salt (e.g. NH$_4$Cl);
  c) hypotonic treatment (at physiological pH);
ii) separation
  d) centrifugation;
  e) sedimentation;
  f) others.

The methods (a) to (e) are briefly described below:
a) Treatment with a surfactant:

This method inhibits subsequent staining, and in addition to lysing of erythrocytes, it causes morphological changes in leukocytes, such as the loss of nuclei, swelling and shrinking, thereby making it difficult to achieve 3-part differentiation of leukocytes by signals of scattered light. Furthermore, leukocytes in the sample treated with a surfactant will experience morphological changes with time.

b) Treatment with an ammonium salt:

This method inhibits subsequent staining. In addition, the ammonium salt does not have a great ability to lyse erythrocytes, and a thick sample that is a 20-fold dilution of the whole blood is difficult to prepare by this method. Furthermore, it takes as many as 3-5 minutes to achieve complete lysis of erythrocytes by method b).

c) Hypotonic treatment:

This method leaves leukocytes intact while lysing erythrocytes by making use of the fact that leukocytes are more resistant than erythrocytes in hypotonic solutions. However, at a physiological pH and under conditions that cause complete lysis of erythrocytes, part of the leukocytes will be destroyed.

d) Centrifugation, e) Sedimentation:

Both methods have such disadvantages as cumbersome and lengthy procedures, and high incidence of leukocyte loss and fluctuations in fractionation ratio.

In all of the methods of the present invention except the one-step method, erythrocytes in a blood sample are disrupted by an acidic and hypotonic treatment such as to reduce the disturbance that occurs in the intensity distribution of right-angle scattered light on account of coincidence of red and white blood cells.

As already mentioned, if a hypotonic treatment is performed in the physiological pH range, not only the erythrocytes but also some leukocytes will be destroyed. On the other hand, if a hypotonic treatment is performed in an acidic pH range, for example, at a pH between 2.0 and 5.0, leukocytes will remain intact and only erythrocytes will be disrupted. In this case, no morphological changes such as the loss of nuclei, swelling and shrinkage will occur in leukocytes.

The mechanism by which erythrocytes are selectively lysed is not clear but as erythrocytes are progressively lysed by hypotonic treatment, embrittlement of their membranes and acidic fixation of leukocytes will probably proceed under acidic pH conditions, with the result that only leukocytes which are more resistant than erythrocytes remain intact.

As a result of this hypotonic treatment under acidic conditions, most of the erythrocytes become "ghosty" and only part of them is reduced to "fragments". As a consequence, the intensity of right-angle scattered light signals from erythrocytes is reduced to no more than a half to a third of the intensity of right-angle scattered light signals from lymphocytes, and the coincidence of red and white blood cells can be disregarded for practical purposes.

Since not all of the erythrocytes are reduced to "fragments" by the hypotonic treatment under acidic conditions, it is difficult to discriminate erythrocytes from leukocytes solely on the basis of the intensity of scattered light signals. Therefore, as already mentioned, it is desirable to discriminate erythrocytes from leukocytes by the intensity of a fluorescence signal.

Erythrocytes cannot be completely discriminated from leukocytes solely on the basis of the intensity of a right-angle scattered light signal, but if the intensity of forward scattered light signals is used as a criterion as in the case of the third method of the present invention, leukocytes can be completely distinguished from erythrocytes or platelets that have been subjected to a hypotonic treatment under acidic conditions. In this case, corpuscles that produce forward scattered light signals having intensities greater than a certain level are picked up as leukocytes that are separate from erythrocytes, platelets or noise.

The functions performed by the stains employed in the methods of the present invention are described hereinafter.

Astrazon Yellow 3G (C.I. No. 48,055 or C.I. Basic Yellow 11) has the following chemical formula:

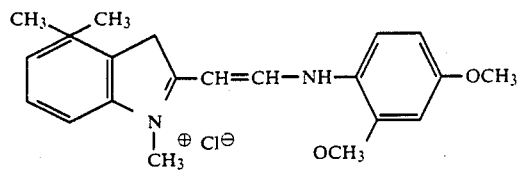

The excitation and fluorescence characteristics of Astrazon Yellow 3G are shown in FIG. 5. This dye has an excitation maximum at 430–455 nm and a fluorescence maximum at 525 nm.

Astrazon Yellow 3G binds with heparin, histamine, histone or protamine in eosinophils and basophils so as to stain granules deeply. This contributes greatly to reduction in the intensity of forward scattered light.

Figure 6:
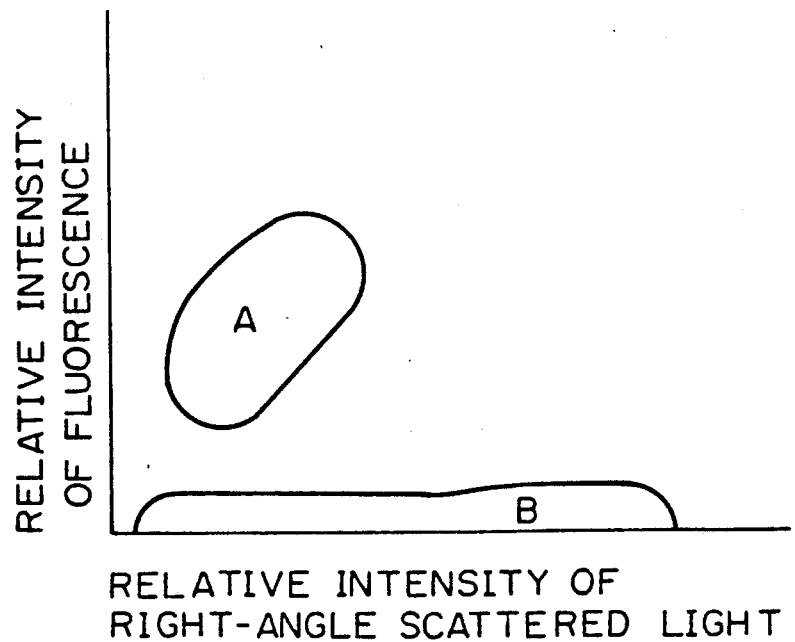
FIGS. 6 and 7 are two-dimensional plots of the intensities of fluorescence and right-angle scattered light from different types of leukocytes stained with Astrazon Yellow 3G.

A two-dimensional plot of the intensities of fluorescence and right-angle scattered light for low concentrations (50–100 ppm) of Astrazon Yellow 3G is shown in FIG. 6, in which A represents basophils; B, other leukocytes; C, eosinophils at an Astrazon Yellow 3G concentration of 400 ppm; and D, eosinophils at an Astrazon Yellow 3G concentration of 200 ppm. As one can see from FIG. 6, only basophils (A) are within a measurable range. The intensity of fluorescence from basophils levels off at an Astrazon Yellow 3G concentration of 100–200 ppm and will not increase at higher concentrations.

Figure 7:
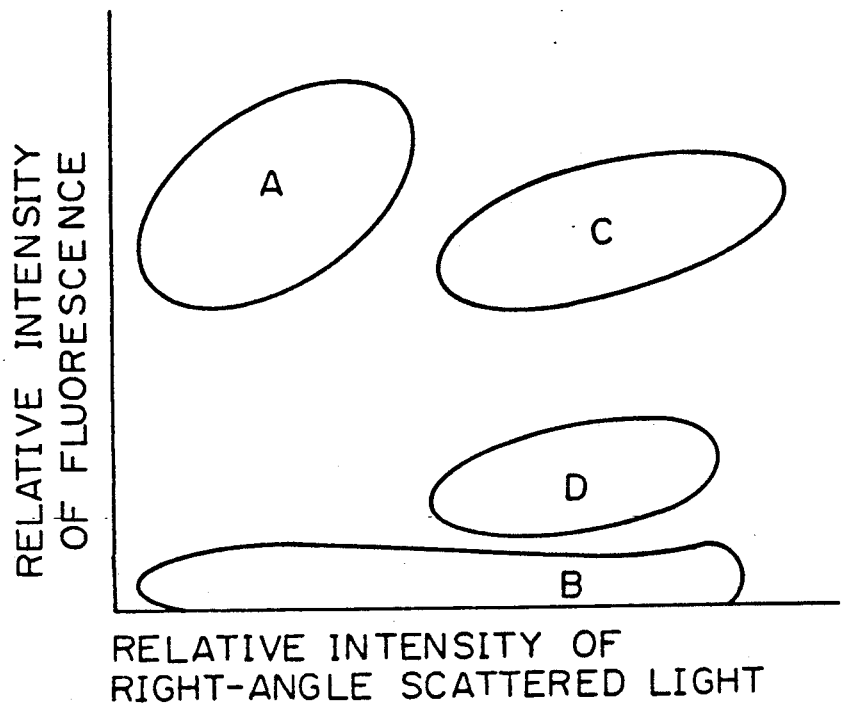

When the concentration of Astrazon Yellow 3G is within the range of 100–200 ppm, not only basophils but also eosinophils can be measured (see D in FIG. 7, wherein the symbols used have the same meanings as defined for FIG. 6) and as the stain concentration increases, the intensity of fluorescence from eosinophils also increases (see C in FIG. 7).

As FIG. 7 also shows, a stain consisting of only Astrazon Yellow 3G is unable to stain lymphocytes, monocytes or neutrophils and therefore is ineffective for producing a total white cell count. It is therefore necessary to add a dye that stains the nuclei of all leukocytes without impairing the staining capability of Astrazon Yellow 3G. All of the dyes listed before that stain the nuclei of leukocytes suit this purpose, but dyes that have an excitation maximum at or near 488 nm are particularly preferable when an argon ion laser is used as the light source 12 of a flow cytometer. One of the dyes that may be selected from this viewpoint is Astrazon Orange R.

Astrazon Orange R has the following chemical formula:

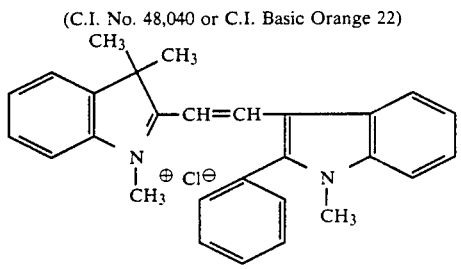

(C.I. No. 48,040 or C.I. Basic Orange 22)

The excitation and fluorescence characteristics of Astrazon Orange R are shown in FIG. 8. This dye has an excitation maximum at 490 nm and a fluorescence maximum at 520 nm.

Figure 9:
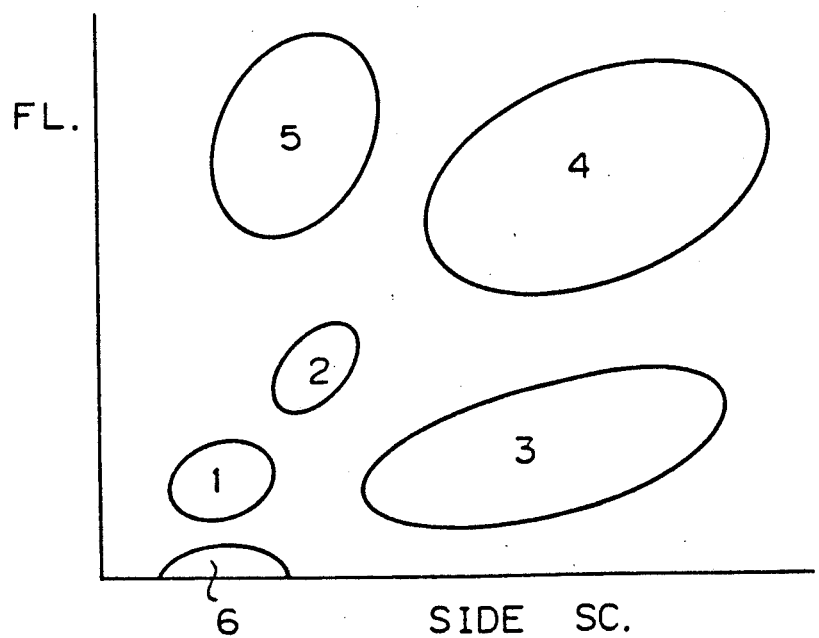
FIG. 9 is a two-dimensional plot of the intensities of fluorescence and right-angle scattered light associated with the classification of leukocytes into five types.

A two-dimensional plot of the intensities of fluorescence and right-angle scattered light when a dye consisting of Astrazon Yellow 3G and Astrazon Orange R is used in leukocyte classification is shown in FIG. 9, in which FL signifies the relative intensity of fluorescence, Sc the relative intensity of right-angle scattered light, 1 to 5 denotes the populations of lymphocytes, monocytes, neutrophils, eosinophils and basophils, respectively, and 6 is a noise component (the same symbols used hereinafter have the same definitions).

As shown in FIG. 9, leukocytes can be classified into five types based on the intensities of fluorescence and right-angle scattered light. Since only one channel needs to be used when Astrazon Yellow 3G is combined with Astrazon Orange R, the dichroic mirror 30, color filter 34 and photomultiplier tube 36 can be eliminated from the optics of the flow cytometer shown in FIG. 1(a) and the resulting apparatus is simpler in composition than the one described in Japanese Patent Application No. 213715/1986.

Leukocytes can also be classified into five distinct types based on the intensities of forward scattered light and right-angle scattered light as shown in FIG. 30(b). Prior to the present invention, this was not possible even if a sample of leukocytes unstained with fluorochromes is classified by a prior art technique based on the measurements of the intensities of forward scattered light and right-angle scattered light. The present inventors have found that only when the intensities of forward scattered light from eosinophils and basophils are reduced can leukocytes be classified into five distinct types solely on the basis of the intensities of forward scattered light and right-angle scattered light.

The compositions, pHs and osmolarities of the dye solutions employed in the methods of the present invention are described below in detail.

One-step method:

(a) Dye concentration

Figure 10:
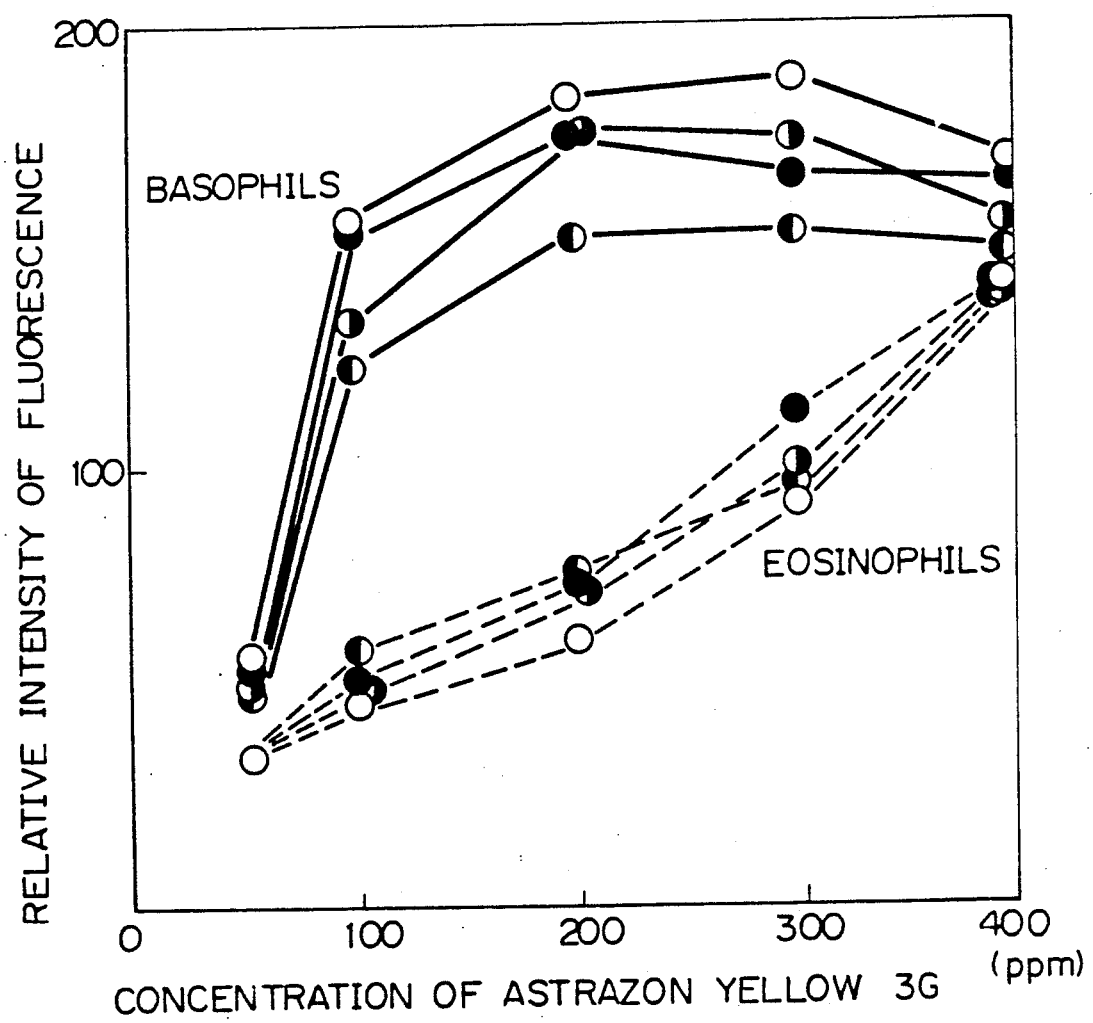
FIG. 10 is a graph showing the dependency of the intensities of fluorescence from eosinophils and basophils on the concentration of Astrazon Yellow 3G.
Figure 11:
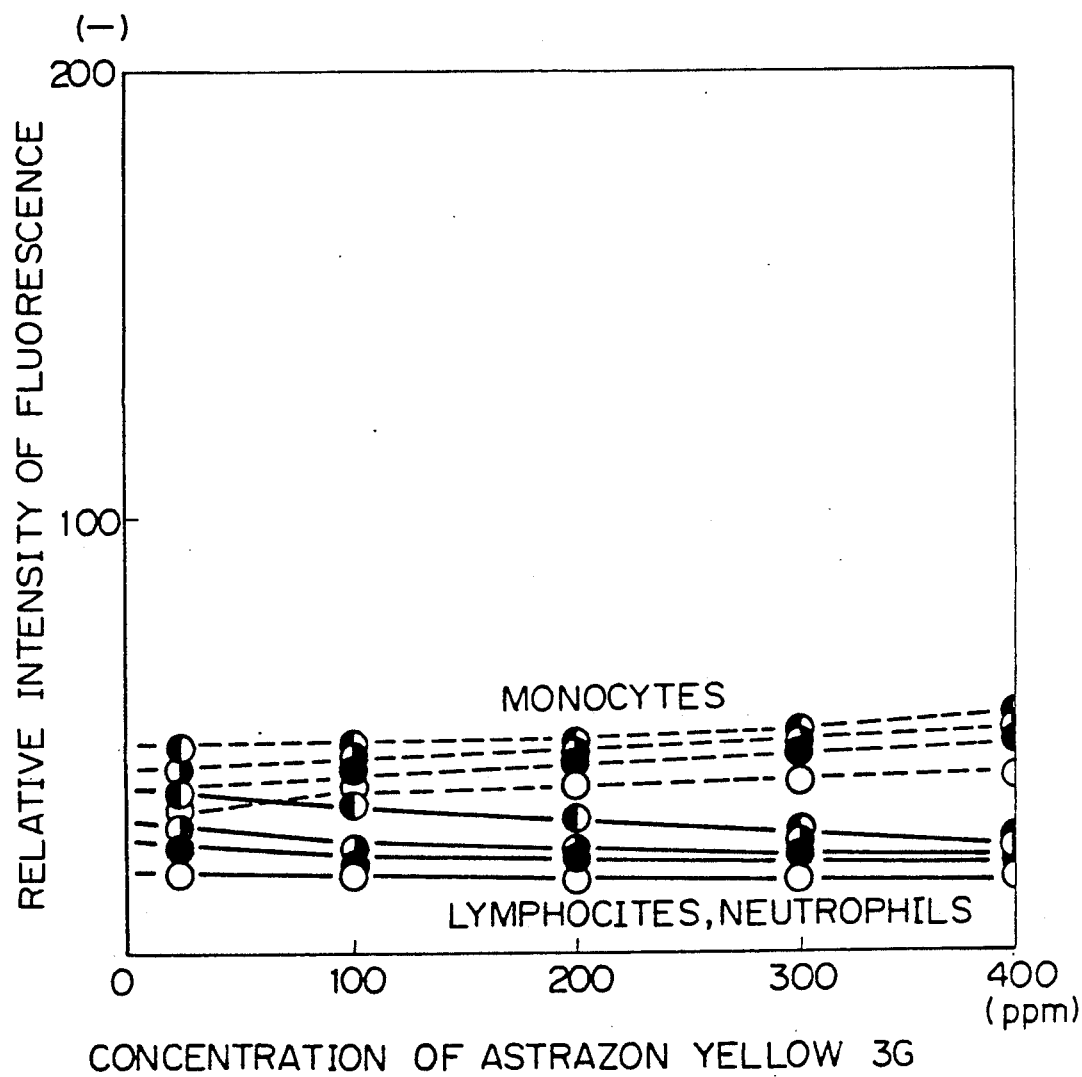
FIG. 11 is a graph showing the dependency of the intensities of fluorescence from lymphocytes, neutrophils and monocytes on the concentration of Astrazon Yellow 3G.

The relative intensities of fluorescence from eosinophils and basophils that were stained with five different concentrations (50, 100, 200, 300 and 400 ppm) of Astrazon Yellow 3G in combination with four different concentrations of Astrazon Orange R (100 ppm, ○; 200 ppm, ●; 300 ppm, ◐; and 400 ppm, ◑) are plotted in FIG. 10, in which the results for basophils are indicated by the solid lines and those for eosinophils by the dashed lines. Plots of the relative intensities of fluorescence from lymphocytes/neutrophils and from monocytes are shown in FIG. 11, in which the results for lymphocytes/neutrophils are indicated by the solid lines and those for monocytes by the dashed lines. As one can see from FIG. 10, the intensity of fluorescence from basophils is higher than that from the other types of leukocytes at Astrazon Yellow 3G concentrations of 100 ppm and above, and the intensity of fluorescence from eosinophils also increases at concentrations of 200 ppm and above. FIG. 11 shows that the intensities of fluorescence from lymphocytes, neutrophils and monocytes are virtually independent of the concentration of Astrazon Yellow 3G. It is therefore concluded that in order to differentiate basophils and eosinophils from the other types of leukocytes in terms of the intensity of fluorescence, the concentration of Astrazon Yellow 3G may be adjusted to 150–200 ppm and higher.

Figure 12:
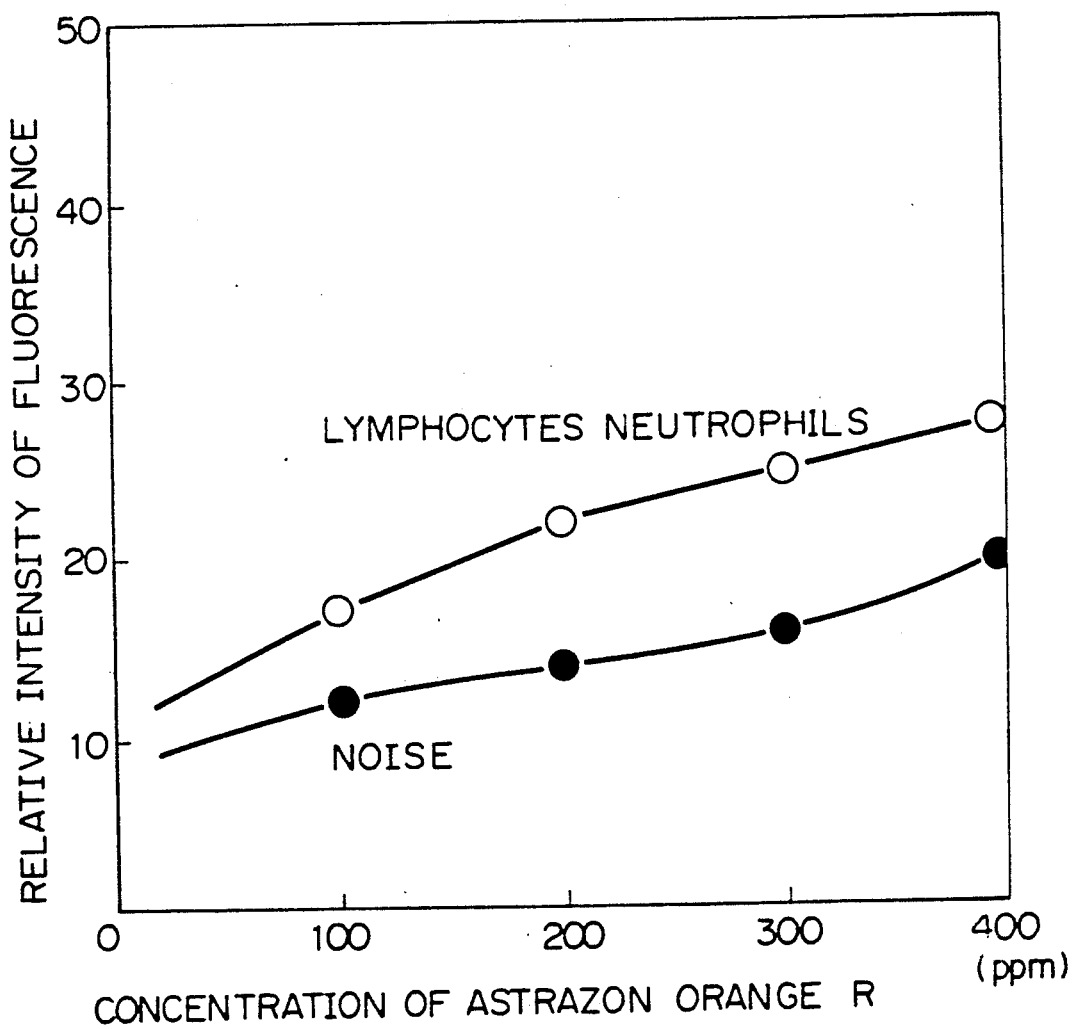
FIG. 12 is a graph showing the dependency of the intensity of fluorescence from lymphocytes/neutrophils on the concentration of Astrazon Orange R (with the concentration of Astrazon Yellow 3G fixed at 300 ppm)

FIG. 12 shows the dependency of the intensity of fluorescence from lymphocytes/neutrophils and the intensity of noise on the concentration of Astrazon Orange R over the range of from 100 to 400 ppm, with the concentration of Astrazon Yellow 3G fixed at 300 ppm. Separation between noise and the intensity of fluorescence from lymphocytes/neutrophils is possible at Astrazon Orange R concentrations of 100 ppm and above, and good separation can be achieved at concentrations of 200 ppm and above. At concentrations of 300 ppm and above, the efficiency of separation substantially levels off and the intensities of fluorescence from basophils and eosinophils decrease slightly (see FIG. 10). Therefore, the concentration of Astrazon Orange R is preferably at 300 ppm or in its neighborhood for achieving efficient separation of leukocytes from noise.

(b) pH

Figure 13:
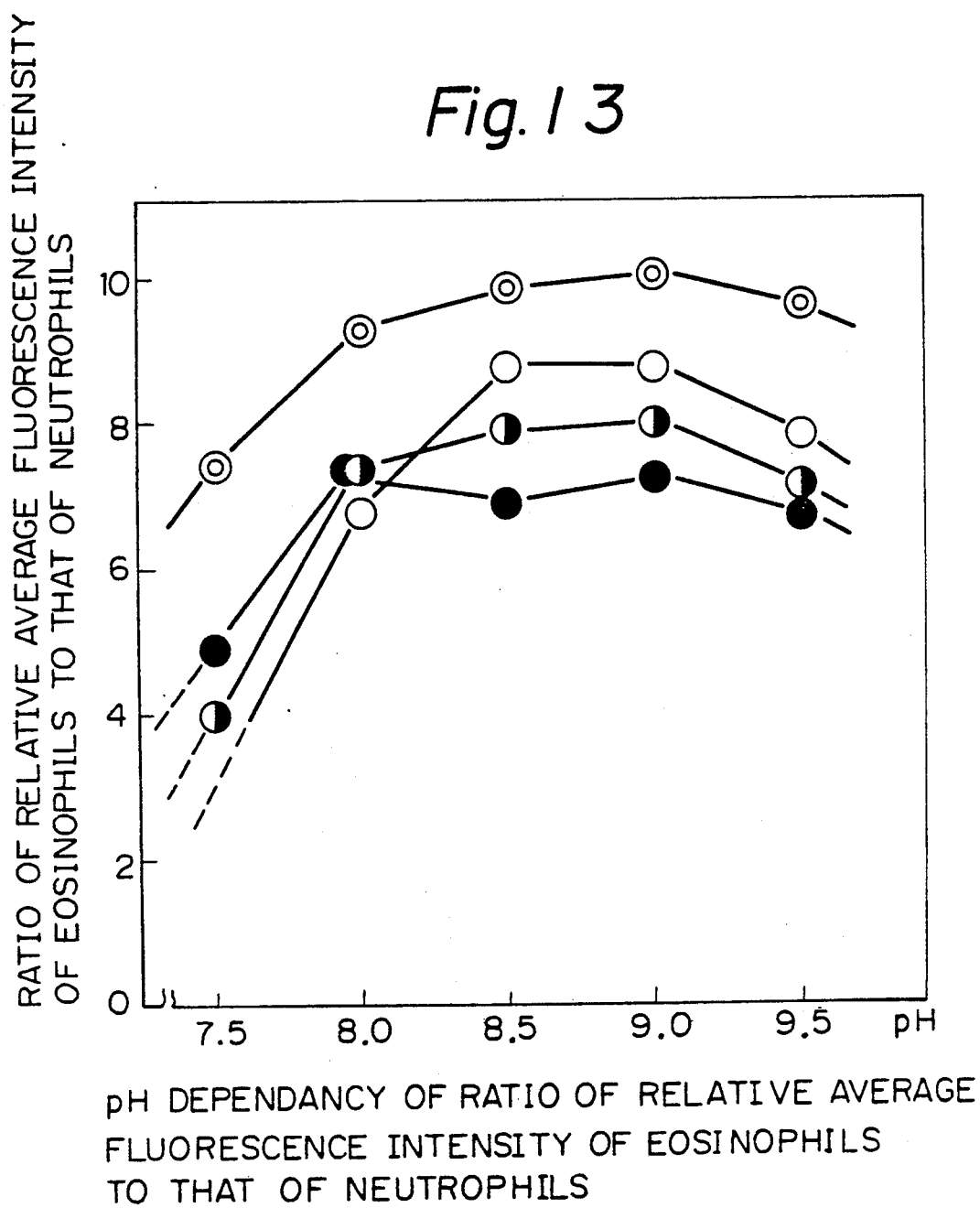
FIG. 13 is a graph showing the profile of the relative intensity of fluorescence from basophils as against neutrophils as a function of the pH of a dye solution.
Figure 14:
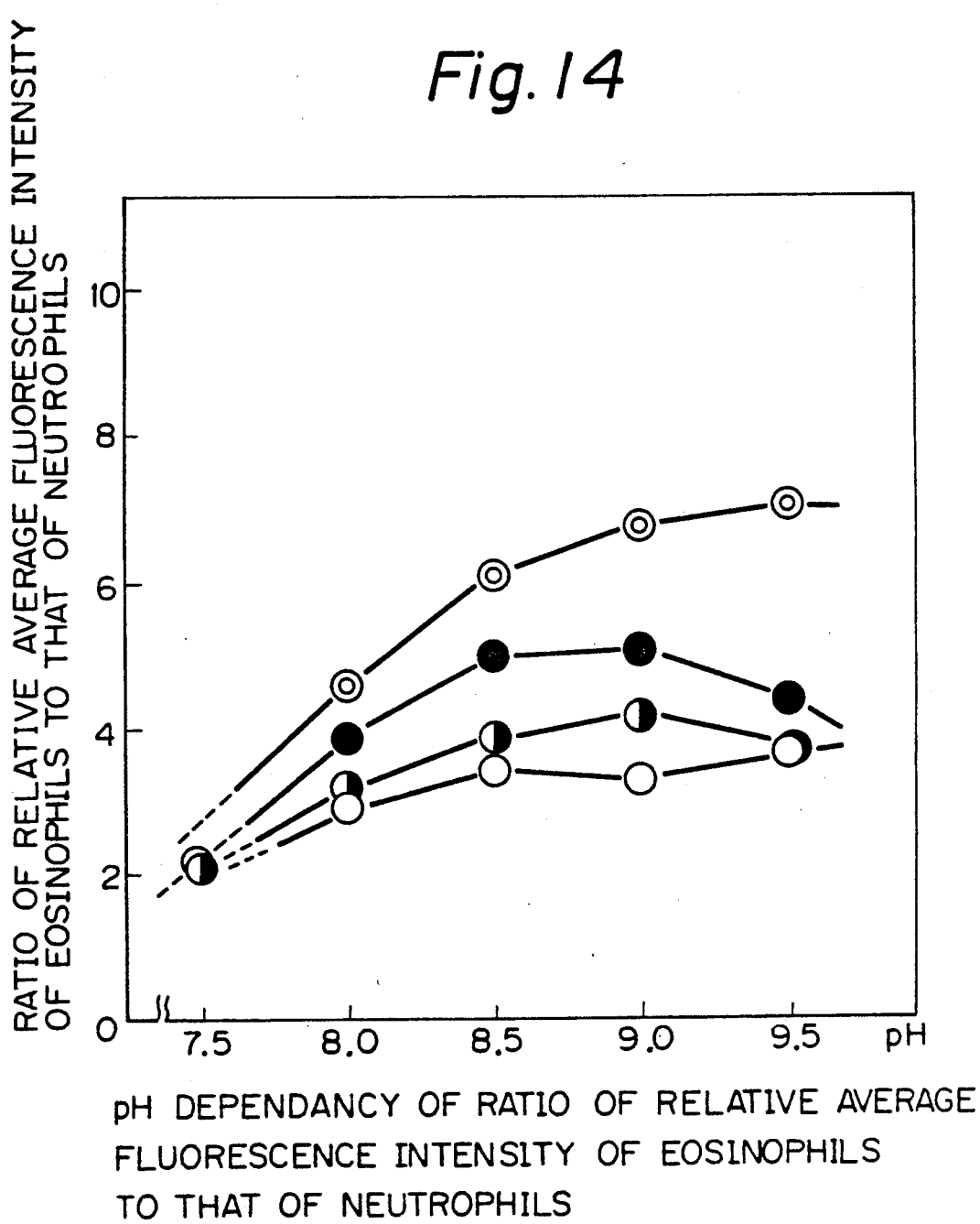
FIG. 14 is a graph showing the profile of the relative intensity of fluorescence from eosinophils as against neutrophils as a function of the pH of a dye solution.

The profile of the relative average intensity of fluorescence from basophils as against neutrophils is shown in FIG. 13 as a function of the pH of the dye solution over the range of from 7.5 to 9.5. The symbols used in FIG. 13 have the following meanings: ○, 100 ppm of Astrazon Yellow 3G in combination with 100 ppm of Astrazon Orange R; ◐, 200 ppm of Astrazon Yellow 3G in combination with 200 ppm of Astrazon Orange R; ●, 300 ppm of Astrazon Yellow 3G in combination with 300 ppm of Astrazon Orange R; ⊙, 350 ppm of Astrazon Yellow 3G in combination with 100 ppm of Astrazon Orange R. The profile of the relative average intensity of fluorescence from eosinophils as against neutrophils is shown in FIG. 14 as a function of the pH of the dye solution over the same range. The symbols used in FIG. 14 have the same meanings as defined for FIG. 13. As one can see from these figures, the relative intensities of fluorescence from basophils and eosinophils as against neutrophils both peak at pHs between 8.5 and 9.0.

(c) Buffer

Useful buffers are glycylglycine, taurine, barate and tricin. It is particularly preferred to use tricin in amounts of 10–100 mM.

(d) Osmolarity compensating agent

The intensity of fluorescence will not change if the concentration of sodium chloride is within the range of 75–225 mM. The use of sodium chloride under an approximately isotonic condition (150 mM) is recommended.

Two-step method:

The final dye concentration to be employed in the two-step method may be set within the range specified for the one-step method. The other conditions to be satisfied are as follows:

(a) pH of the first fluid

In order to lyse erythrocytes, the pH of the first fluid is preferably set at 5.0 and below, but in order to prevent coagulation of platelets, the pH of the first fluid must be at least 3.5. A particularly suitable value is 4.5.

(b) Buffer in the first fluid

Any buffer that has a pKa value of approximately 4.5, such as citrate, maleate and diglycolate, may be employed in the first fluid. As for diglycolic acid, the intensity of fluorescence from basophils will decrease slightly if the concentration of diglycolic acid is 5 mM and below. On the other hand, the lysing of erythrocytes will be insufficient if the concentration of diglycolic acid is 50 mM and above. An optimum concentration of diglycolic acid is about 10 mM.

(c) Osmolarity of the second fluid

There will be no change in the separation pattern even if the final osmolarity of the dye solution is varied from 167 to 387 mOsm/kg by changing the amount of an osmalarity compensating agent (e.g. sodium chloride) added to the second fluid. It is recommended that the osmolarity of the second fluid be adjusted in such a way that the final osmolarity of the dye solution is at an approximately isotonic value (280 mOsm/kg).

(d) Buffer in the second fluid

Any buffer that has a pKa value in an approximate range of 8.5 to 9.0, such as borate, Tris and tricin, may be employed in the second fluid. If tricin is used, the intensity of fluorescence from basophils and eosinophils decreases at a tricin concentration of 50 mM and below. A preferred concentration of tricin is 300 mM.

The present invention is hereunder described with reference to examples that were carried out under most preferred conditions. It should however be noted that these examples are by no means intended to limit the present invention.

EXAMPLE 1

One-step Method

Reagents:

| Reagents: | | |
|---|---|---|
| Astrazon Yellow 3 G | (selective dye for basophils and eosinophils) | 350 ppm |
| Astrazon Orange R | (fluorochrome dye for staining the nuclei of leukocytes) | 300 ppm |
| Tricin-sodium hydroxide | (buffer) | 30 mM |
| Sodium chloride | (osmolarity adjusting agent) | 115 mM |
| pH, 8.7; osmolarity, 280 mOsm/kg | | |

Staining procedure:

Twenty parts by volume of the dye solution was added to one part by volume of EDTA 2K anti-coagulated blood. After agitation, the mixture was incubated at 25° C. for about 1 minute.

| Selection of filter and dichroic mirror: | | |
|---|---|---|
| Dichronic mirror 22 | (reflects wavelengths not longer than 510 nm and transmits any unreflected light) | 510 nm |
| Color filter 40 | (transmits wavelengths not shorter than 520 nm) | 520 nm |

Figure 15:
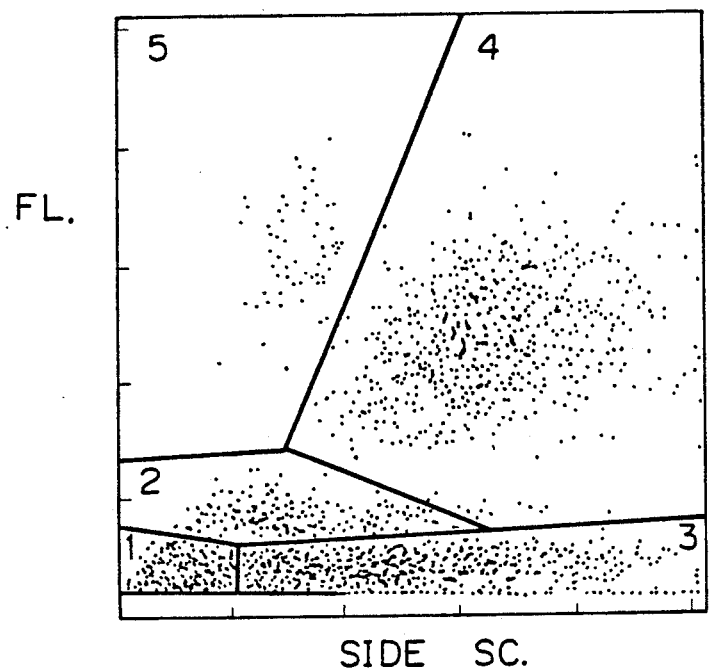
FIG. 15 is a two-dimensional plot of the intensities of fluorescence and right-angle scattered light that is constructed from the results of Example 1 relating to the one-step method of the present invention.

Results of analysis:

A two-dimensional plot of the intensities of fluorescence and right-angle scattered light as measured with a flow cytometer under the conditions described above is shown in FIG. 15. Leukocytes were successfully classified into five types except that there was some overlap between the distributions of lymphocytes (zone 1) and neutrophils (zone 3). This was because the right-angle scattered light was disturbed by the coincidence of erythrocytes and leukocytes.

EXAMPLE 2

Two-step Method

Reagents:

| Reagents: | | |
|---|---|---|
| 1 First fluid | | |
| Astrazon Yellow 3 G | (selective dye for basophils and eosinophils) | 385 ppm |
| Astrazon Orange R | (fluorochrome dye for staining the nuclei of leukocytes) | 330 ppm |
| Diglycolic acid/sodium hydroxide | (buffer) | 10 mM |
| pH, 4.5; osmolarity, 50 mOsm/kg | | |
| 2 Second fluid | | |
| Tricin-sodium hydroxide | (buffer) | 300 mM |
| Sodium chloride | (osmolarity adjusting agent) | 750 mM |
| pH, 9.8–9.9; osmolarity, 2,200 mOsm/kg | | |

Staining procedure:

Eighteen parts by volume of the first fluid was added to one part by volume of EDTA 2K anti-coagulated blood. After agitation, the mixture was incubated at 25° C. for 20 seconds. Thereafter, 2 parts by volume of the second fluid was added and, after agitation, the mixture was incubated at 25° C. for 40 seconds. The finally attained staining conditions were a pH of 8.6–8.7 and an osmolarity of 286 m Osm/kg (isotonic).

Selection of filter and dichroic mirror:

Same as in Example 1.

Results of analysis:

A two-dimensional plot of the intensities of fluorescence and right-angle scattered light as measured with a flow cytometer under the conditions described above is shown in FIG. 16. Leukocytes were successfully classified into five types, and unlike in Example 1, there was no slight overlap between the distributions of lymphocytes (zone 1) and neutrophils (zone 3). This was because all erythrocytes were lysed to eliminate any effects of the coincidence of erythrocytes and leukocytes.

Figure 16:
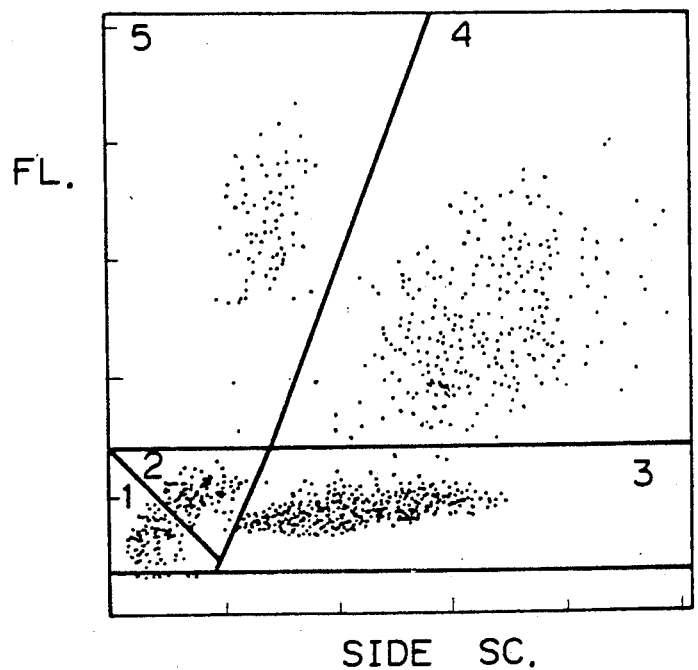
FIGS. 16 and 22 are two-dimensional plots of the intensities of fluorescence and right-angle scattered light that are constructed from the results of Example 2 relating to the two-step method of the present invention.
Figure 17:
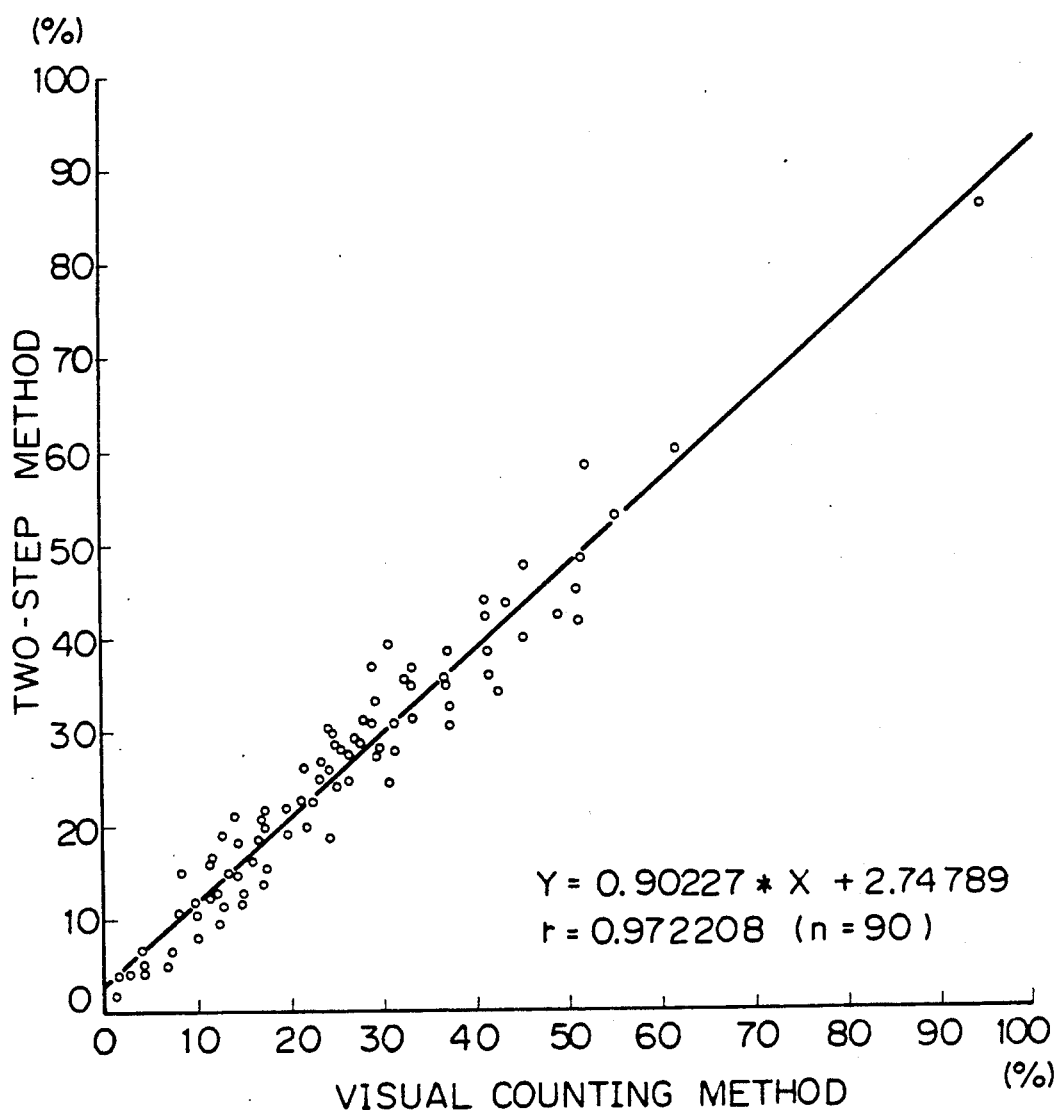
FIG. 17 shows the correlation between the visual counting method and the two-step method of the present invention which employs fluorescence and right-angle scattered light to determine the percentage of lymphocytes in the leukocytes of interest.
Figure 18:
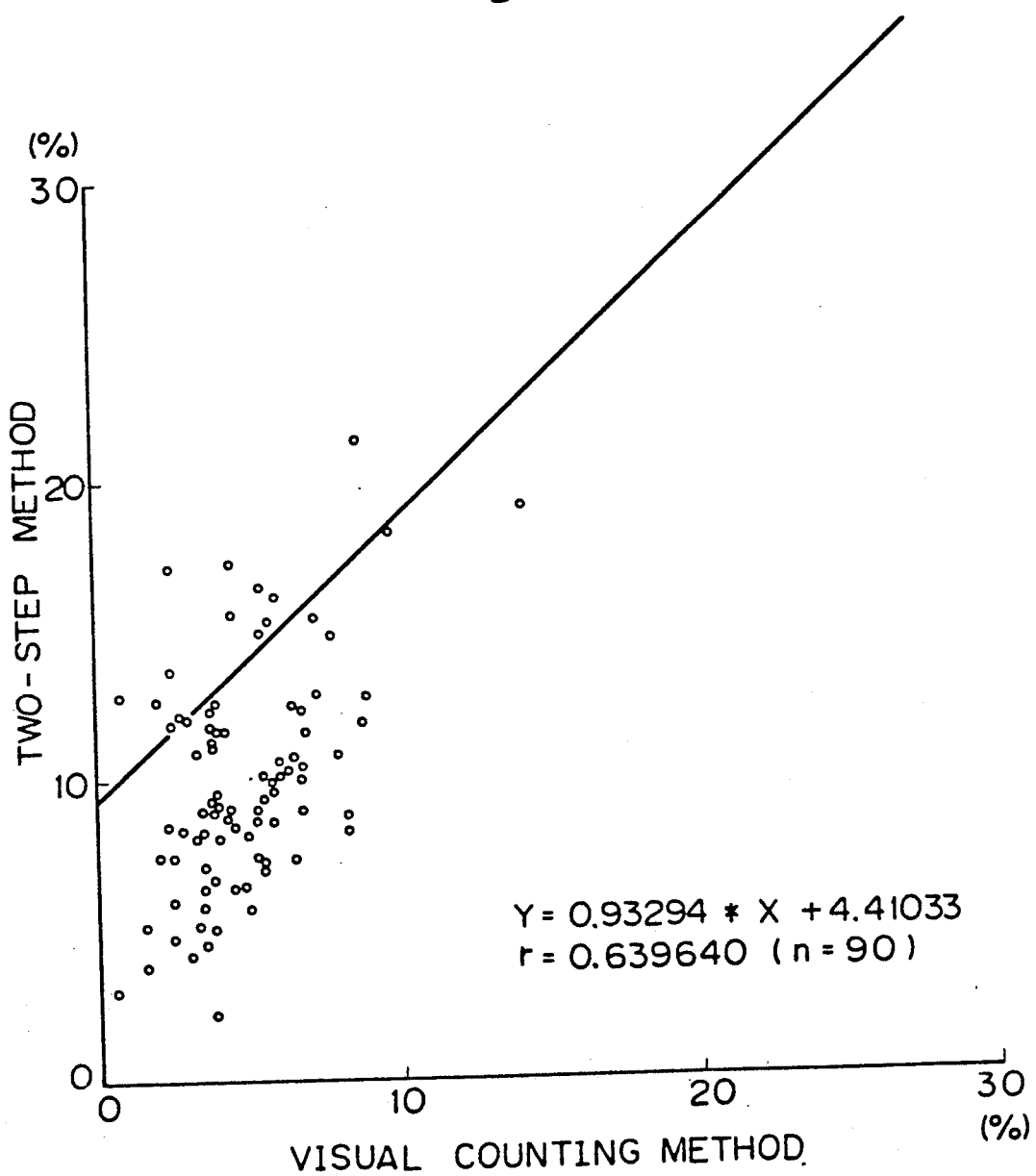
FIGS. 18 to 21 show the results of similar analyses of regression conducted for the percentages of monocytes, neutrophils, eosinophils and basophils, respectively.
Figure 19:
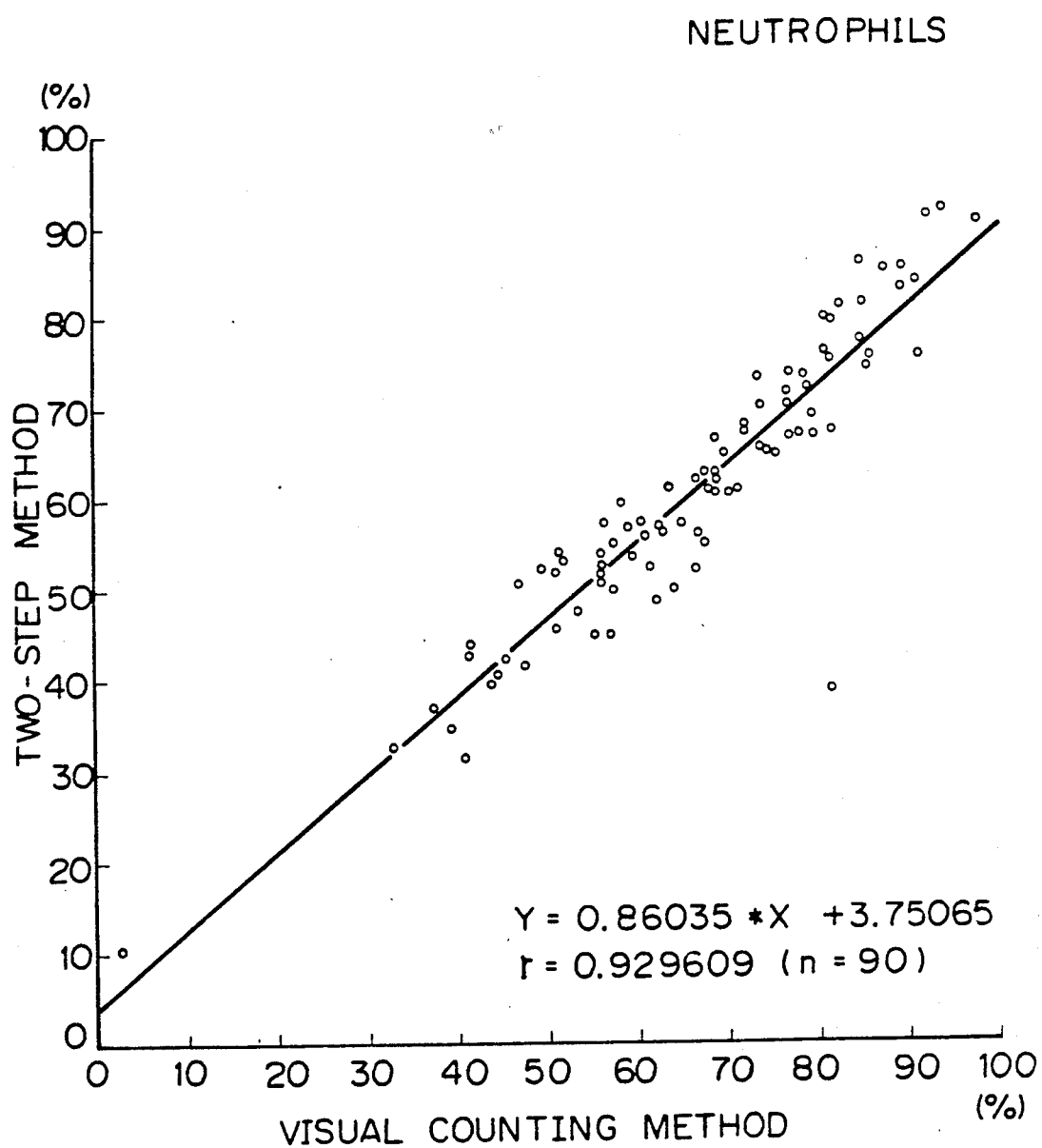
Figure 20:
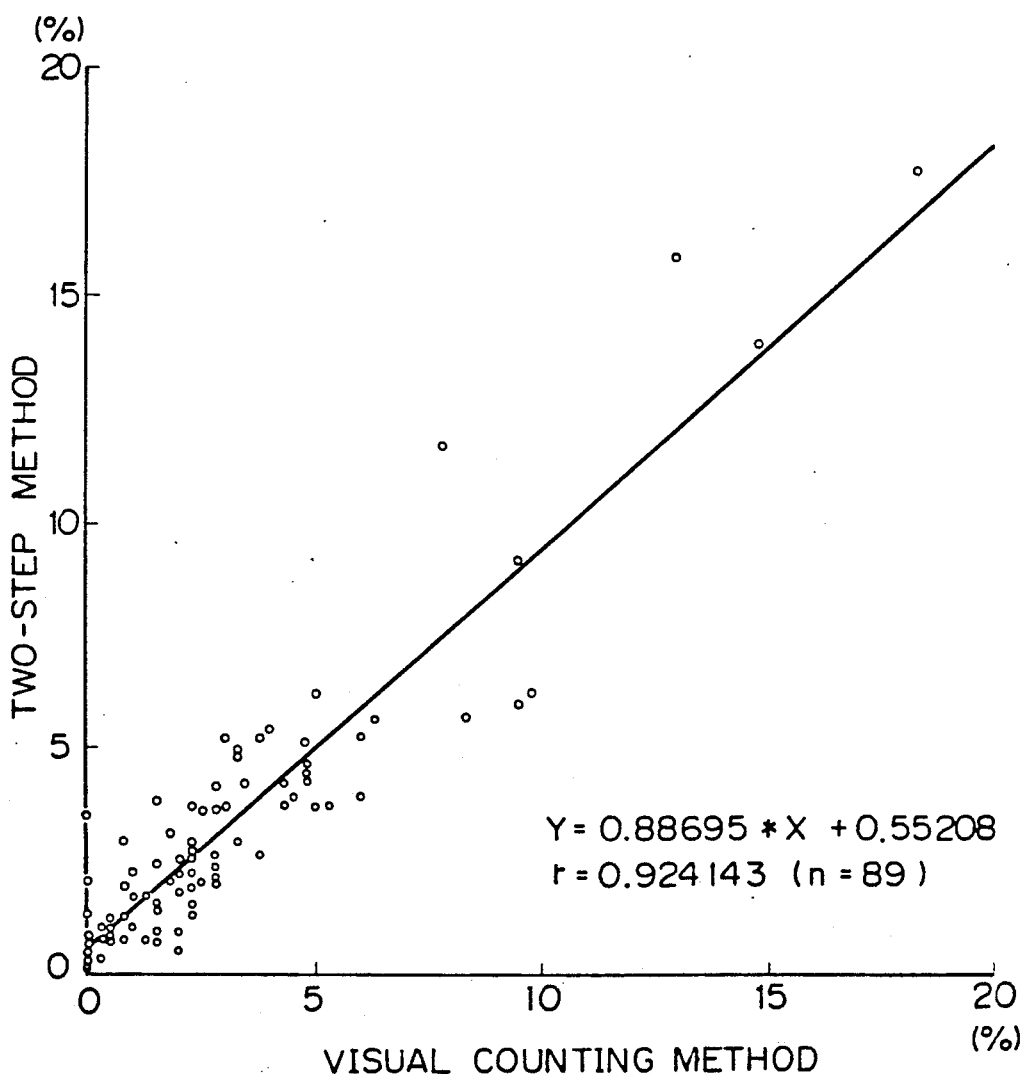
Figure 21:
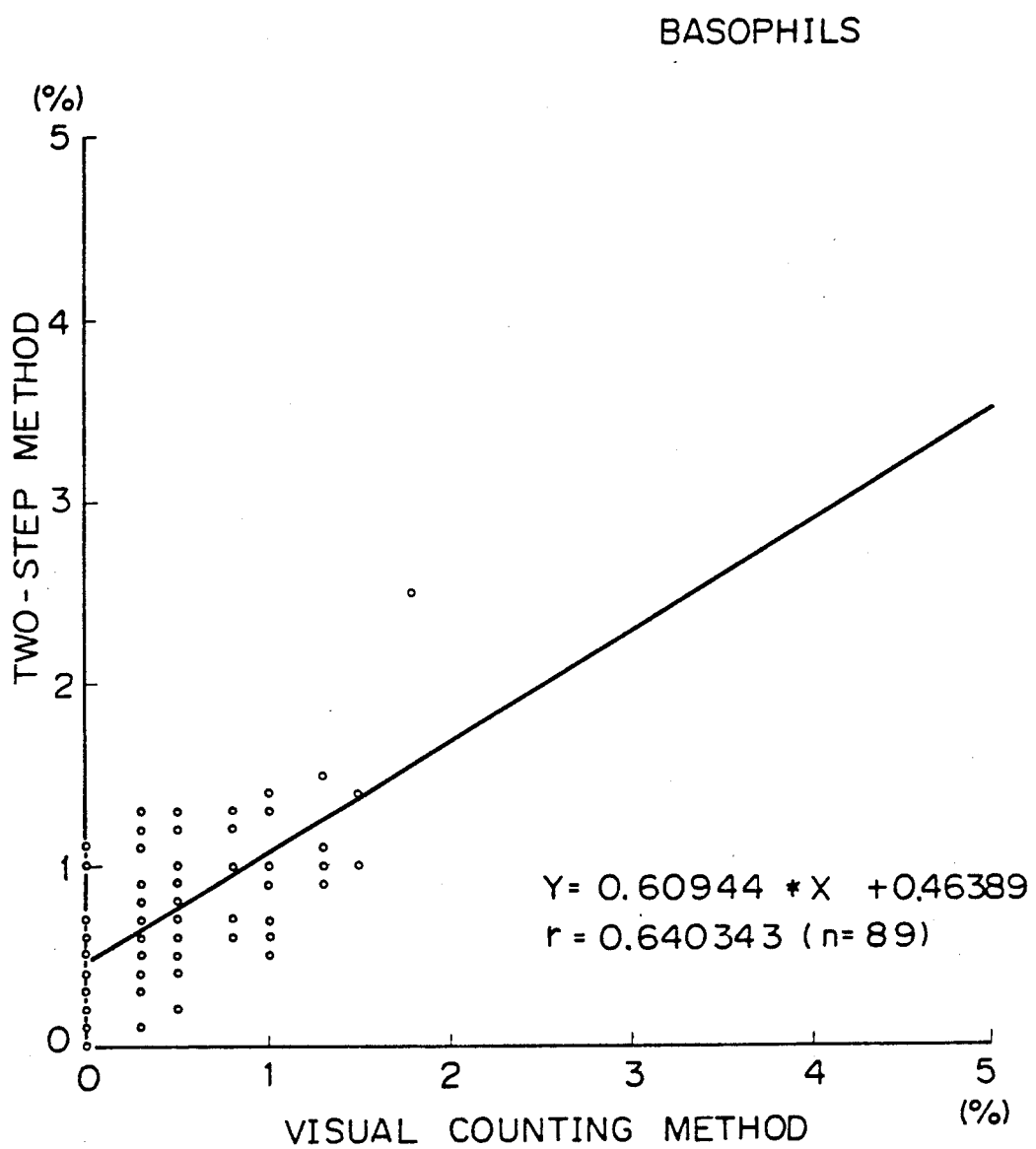

The correlation between the two-step method and the visual counting method may be illustrated by FIGS. 17–21. FIG. 17 shows the correlation between the two methods applied to measure the percentage of lymphocytes in the leukocytes of interest (an example of the data obtained by the two-step method based on the measurement of intensities of fluorescence and right-angle scattered light is shown in FIG. 16). The percentage of lymphocytes counted by the visual method is plotted on the X-axis and that counted by the two-step method is plotted on the Y-axis. The straight line in FIG. 17 is the regression line and the regression of Y upon X is estimated by the equation $Y = 0.90227*X + 2.74789$; r is the correlation coefficient and n is the number of samples. The results of similar analyses of regression conducted for the percentages of monocytes, neutrophils, eosinophils and basophils are graphed in FIGS. 18 to 21, respectively.

The peculiar effects of the two-step method as manifested notably in Example 2 are described below.

Figure 22:
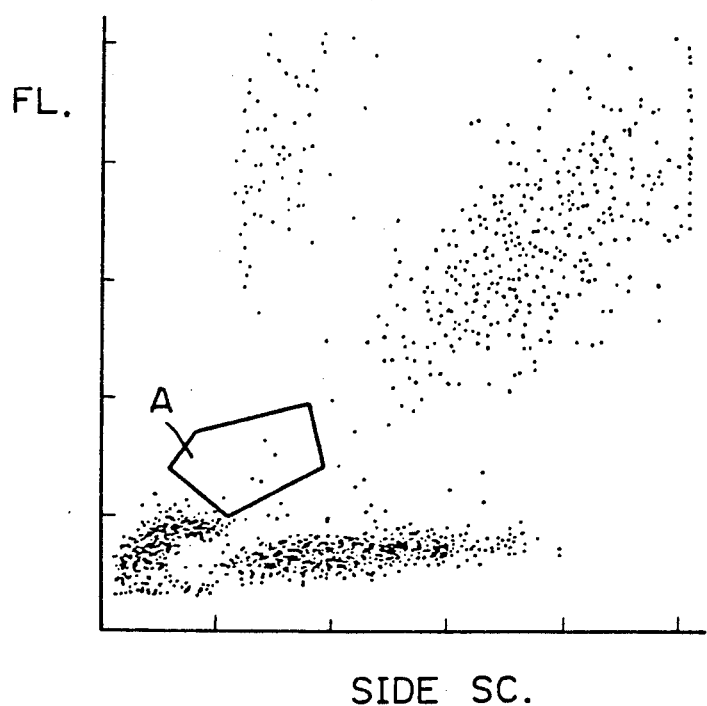

FIG. 22 shows a two-dimensional plot of the intensities of fluorescence and right-angle scattered light that were measured for fresh blood (within 6 hours after sampling) under the conditions employed in Example 2. Apparently, few leukocytes are distributed in zone A. However, when the same measurement was conducted under the same conditions with the exception that the blood had been left to stand for 22 hours after sampling, a population of cells which had not been previously observed occurred in zone A, as shown in FIG. 23. On the basis of the procedures described below, this population was conjectured to have originated from dead neutrophilic cells.

In the first step, to the blood that had been left to stand for 22 hours after sampling, fluorescein diacetate (FDA) capable of selective staining of live cells was added at five different concentrations, 1 ppm, 2 ppm, 5 ppm, 10 ppm and 20 ppm. FIGS. 24 to 28 show two-dimensional plots of the intensities of fluorescence and side-angle scattered light for the respective cases. One can readily see from these figures that in the presence of varying concentrations of FDA, the population in zone A did not change in position, but the other leukocytes (stained with FDA) did. It can therefore be safely concluded that the population in zone A was composed of dead cells.

In the next step, the time-dependent changes in the number of neutrophils in a certain sample (sample 1) and the number of cells in the unknown population were plotted and the results are shown in FIG. 29. As the sample was left to stand for an increased period of time, the percentage of neutrophils (designated by ●) decreased whereas the percentage of cell counts in the unknown population (designated by ○) increased. The percentage of neutrophils as combined with the number of cells in the population at issue remained substantially constant over time, as indicated by ○. The same results were observed for the combined percentage of neutrophils and cells in the population at issue in leukocytes in two other samples (sample 2 designated by ⊙, and sample 3 designated by ◐). Based on the results obtained by the above procedures, it is conjectured that the population in zone A consisted of dead neutrophilic cells.

Dead cells which occur in samples that have been left to stand for a prolonged time are sometimes unaccountable by conventional flow cytometric techniques. In accordance with the two-step method of the present invention, the correct number of neutrophils that would occur if the sample were fresh can be attained by adding the number of cells in zone A to the counts of neutrophils assigned to their inherent zone.

Leaving blood samples to stand for a prolonged time is undesirable not only for the purpose of counting leukocytes but also for measuring other blood parameters. Therefore, if the counts of cells in zone A exceed a predetermined level, it is recommended that an alarm is automatically produced to warm the technician that the sample has been left to stand too long.

EXAMPLE 3

Third Method

Reagents:

| Reagents: | | |
|---|---|---|
| 1 First fluid | | |
| Astrazon Yellow 3 G | (substance capable of selective reduction in the intensity of forward scattered light from basophils and eosinophils) | 385 ppm |
| Astrazon Orange R | (fluorochrome for staining the nuclei of leukocytes) | 330 ppm |
| Diglycolic acid/sodium hydroxide pH, 4.5; osmolarity, 50 mOsm/kg | (buffer) | 10 mM |
| 2 Second fluid | | |

| -continued | | |
|---|---|---|
| Reagents: | | |
| Tricin-sodium hydroxide | (buffer) | 300 mM |
| Sodium chloride | (osmolarity adjusting agent) | 750 mM |
| pH, 9.8–9.9; osmolarity, 2,200 mOsm/kg | | |

Reaction procedures:

Eighteen parts by volume of the first fluid was added to 1 part by volume of EDTA 2K anti-coagulated blood. After agitation, the mixture was incubated at 25° C. for 20 seconds. Thereafter, 2 parts by volume of the second fluid was added and, after agitation, the mixture was incubated at 25° C. for 40 seconds. The finally attained reaction conditions were a pH of 8.6–8.7 and an osmolarity of 286 mOsm/kg (isotonic).

Selection of filter and dichronic mirror:

Same as in Example 1.

Results of analyses:

A two-dimensional plot of the intensities of fluorescence and right-angle scattered light as measured with a flow cytometer under the conditions described above is shown in FIG. 30(a). Leukocytes were successfully classified into five types. The fractions of the individual leukocyte types shown in FIG. 30(a) are classified in FIG. 30(b) according to the intensities of forward scattered light and right-angle scattered light. In obtaining the data shown in FIGS. 30(a) and 30(b), discrimination of leukocytes from noise and from other corpuscles including their ghosts was achieved by means of a fluorescence signal.

Figure 31A:
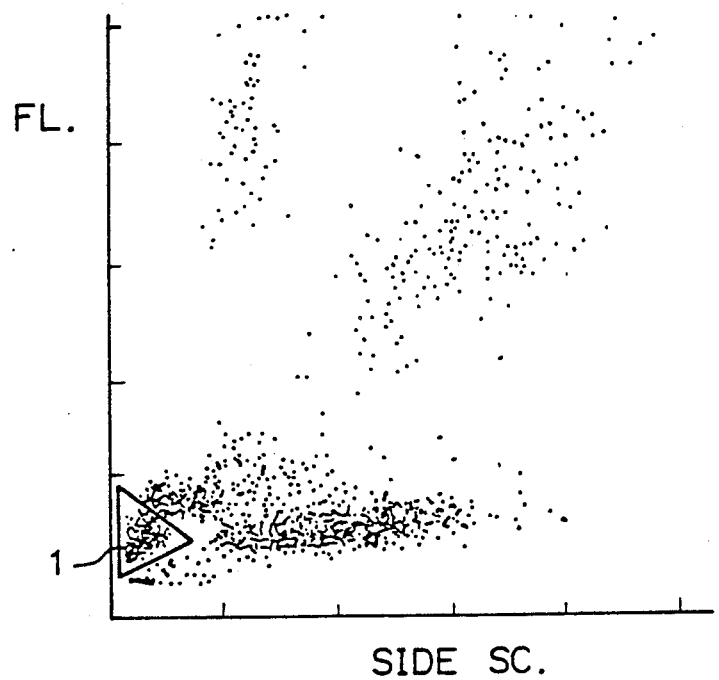
FIG. 31(a) is a graph in which the fraction of lymphocytes shown in FIG. 30(a) is delineated.
Figure 31B:
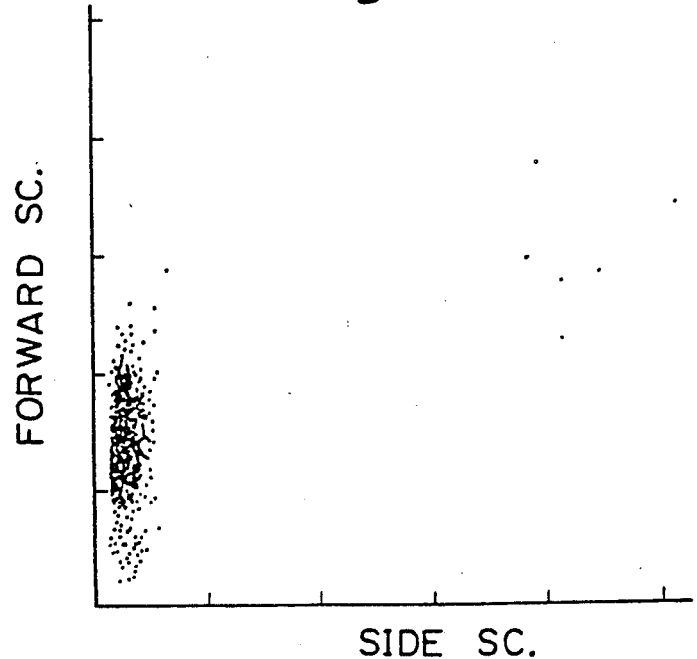
FIG. 31(b) is a graph representing only the signal assigned to that fraction of lymphocytes in terms of the intensities of forward scattered light and right-angle scattered light.
Figure 32A:
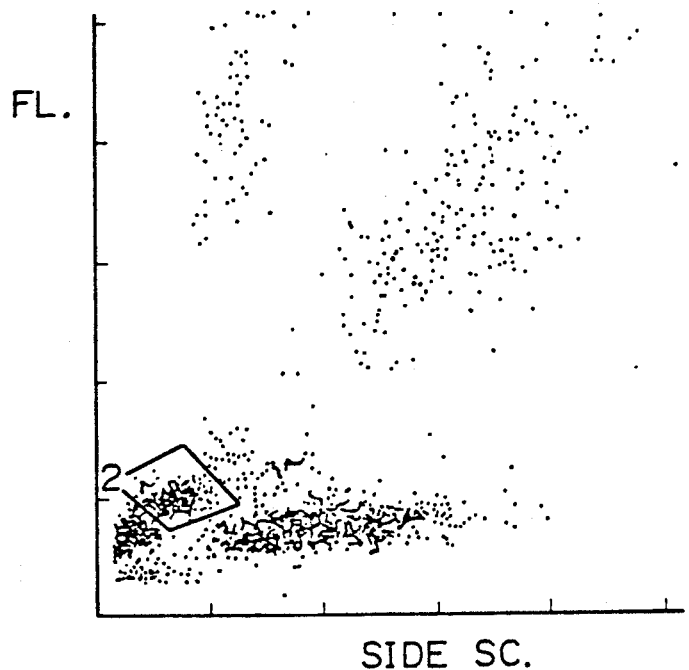
FIGS. 32(a), 33(a), 34(a) and 35(a) are graphs in which the fractions of monocytes, neutrophils, eosinophils and basophils shown in FIG. 30(a) are respectively delineated.
Figure 32B:
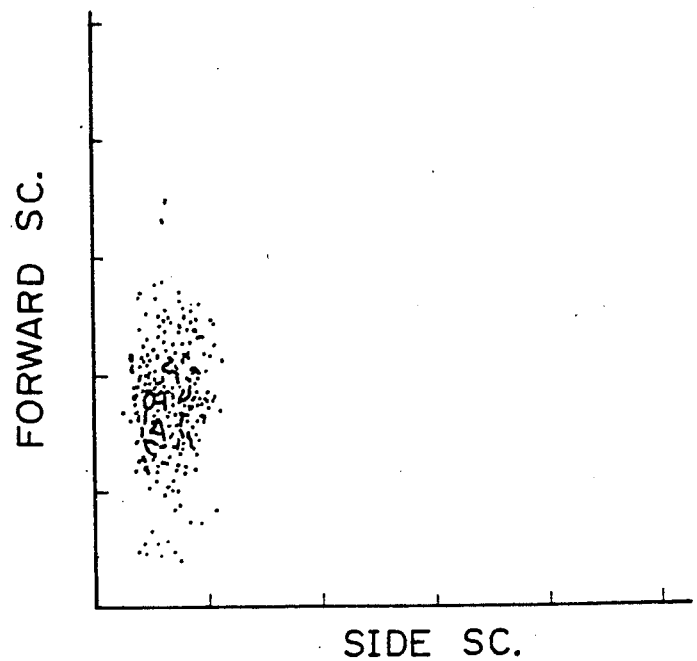
FIGS. 32(b), 33(b), 34(b) and 35(b) are graphs showing the respective four fractions in terms of the intensities of forward scattered light and right-angle scattered light.
Figure 33A:
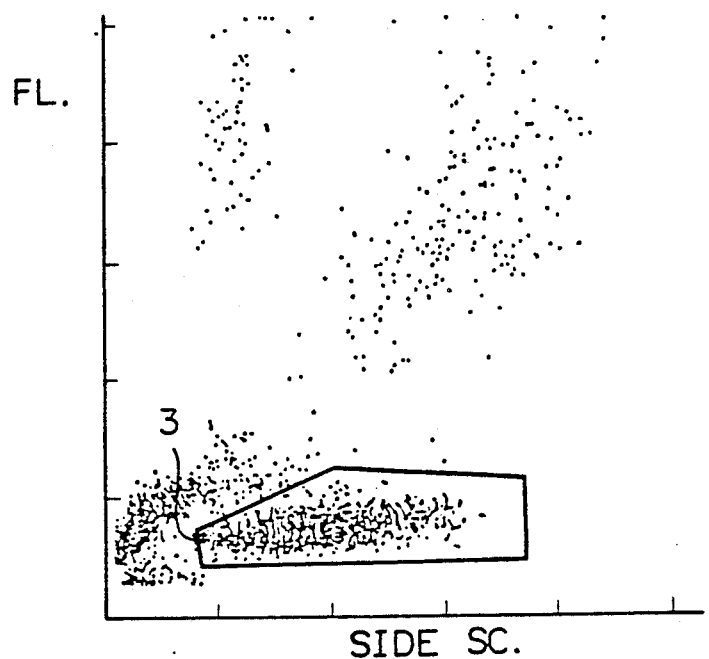
Figure 33B:
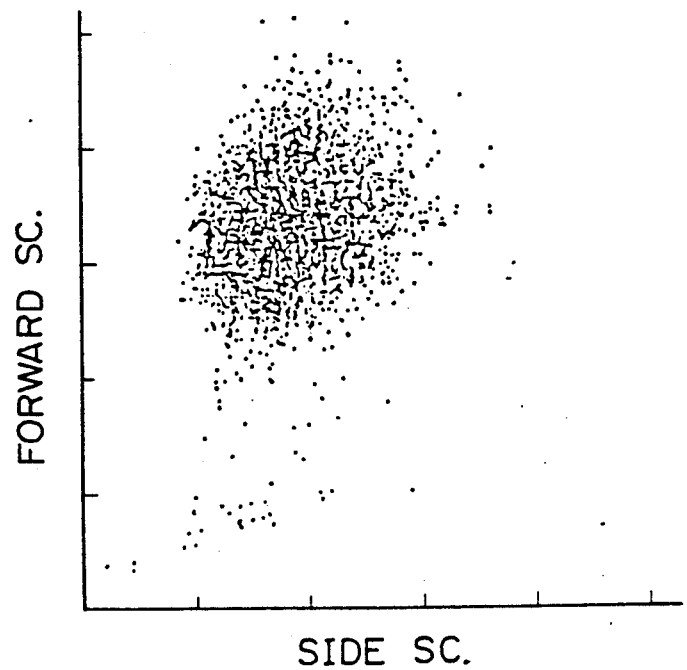
Figure 34A:
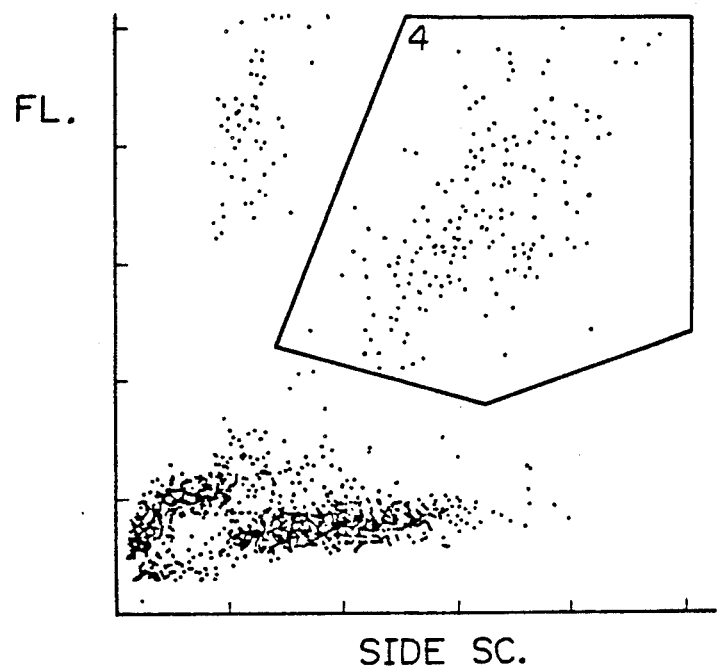
Figure 34B:
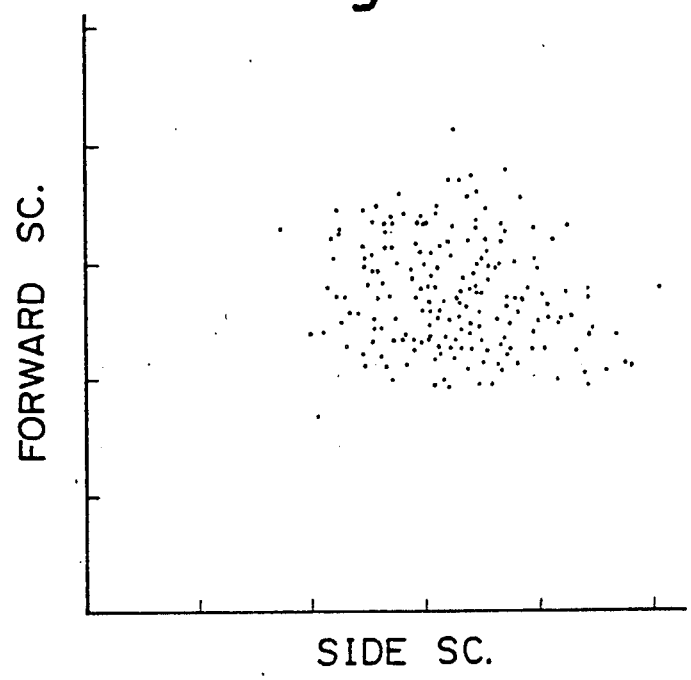
Figure 35A:
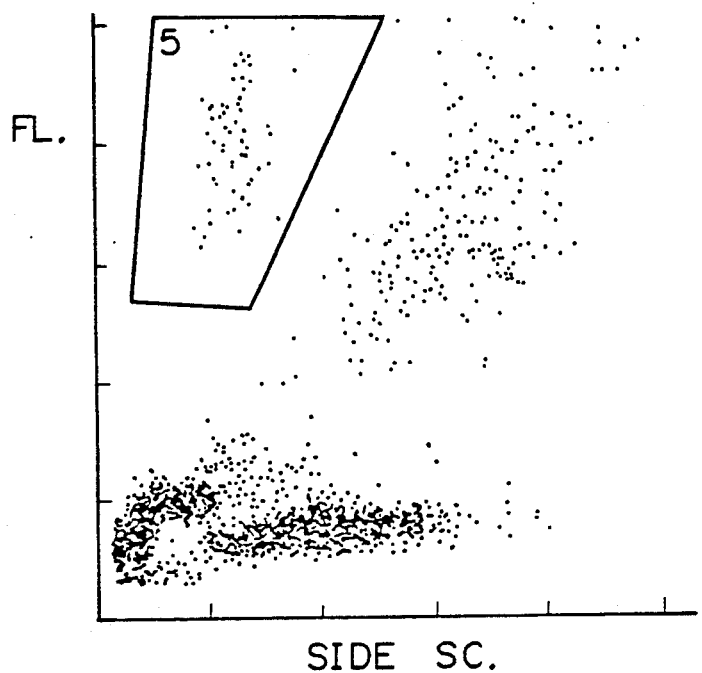
Figure 35B:
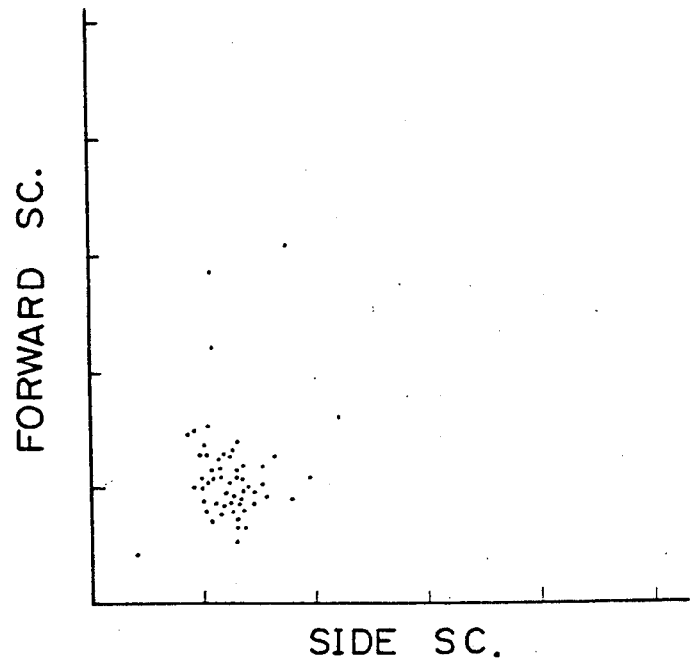

The fraction of lymphocytes shown in FIG. 30(a) is delineated in FIG. 31(a), and only the signal assigned to that fraction is represented in FIG. 31(b) by the intensities of forward scattered light and right-angle scattered light. In a similar manner, the fractions of monocytes, neutrophils, eosinophils and basophils shown in FIG. 30(a) are delineated in FIGS. 32(a), 33(a), 34(a) and 35(a), respectively, and corresponding plots of the intensities of forward scattered light and right-angle scattered light for the respective fractions are shown in FIGS. 32(b), 33(b), 34(b) and 35(b).

The symbols and numerals used in FIGS. 30–35 have the following meanings: FL, relative intensity of fluorescence; Side Sc., relative intensity of right-angle scattered light; Forward Sc., relative intensity of forward scattered light; 1, lymphocyte; 2, monocyte; 3, neutrophil; 4, eosinophil; 5, basophil.

Figure 36:
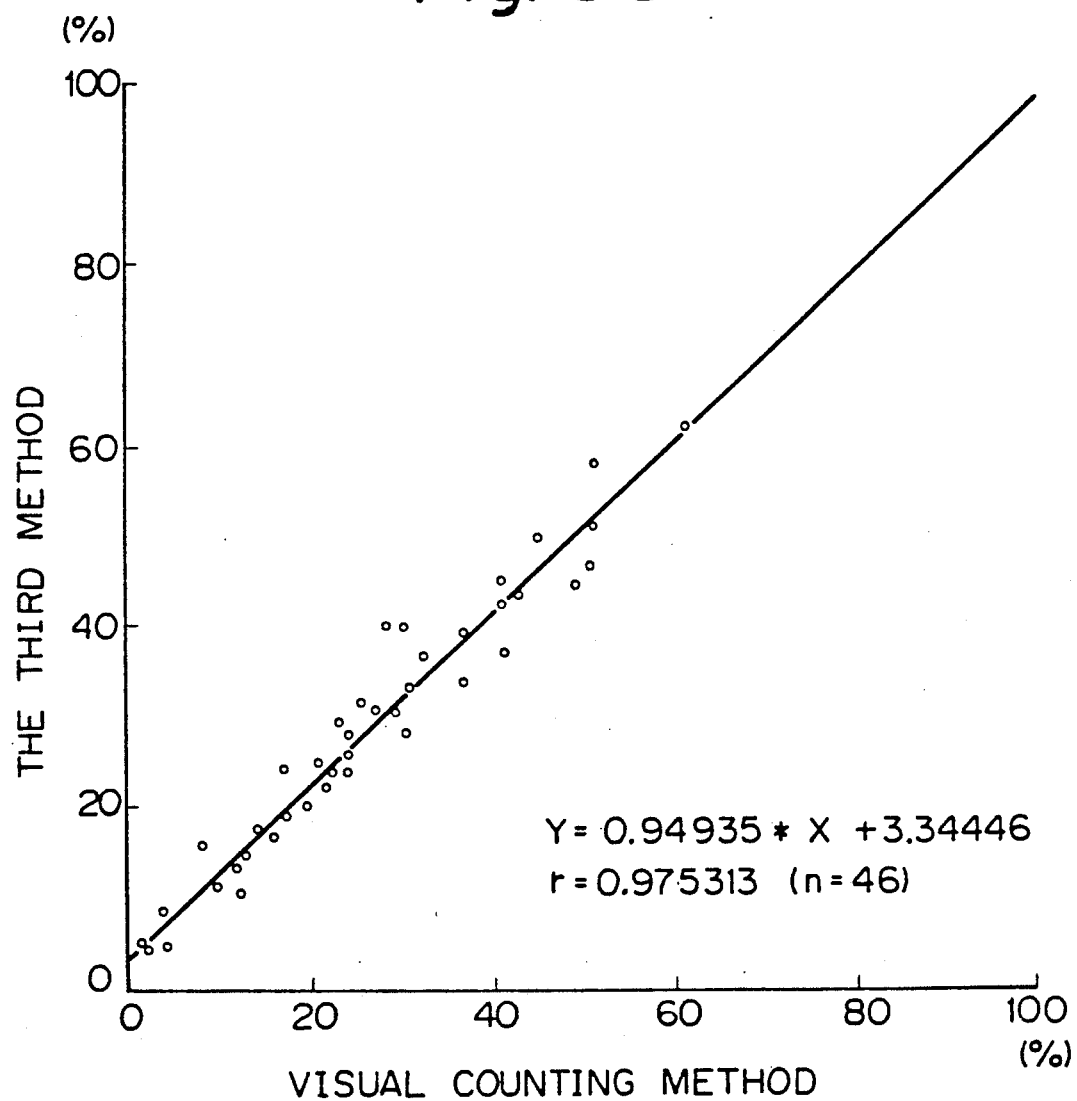
FIG. 36 shows the correlation between the visual counting method and the third method of the present invention which employs forward scattered light and right-angle scattered light to determine the percentage of lymphocytes in the leukocytes of interest.
Figure 37:
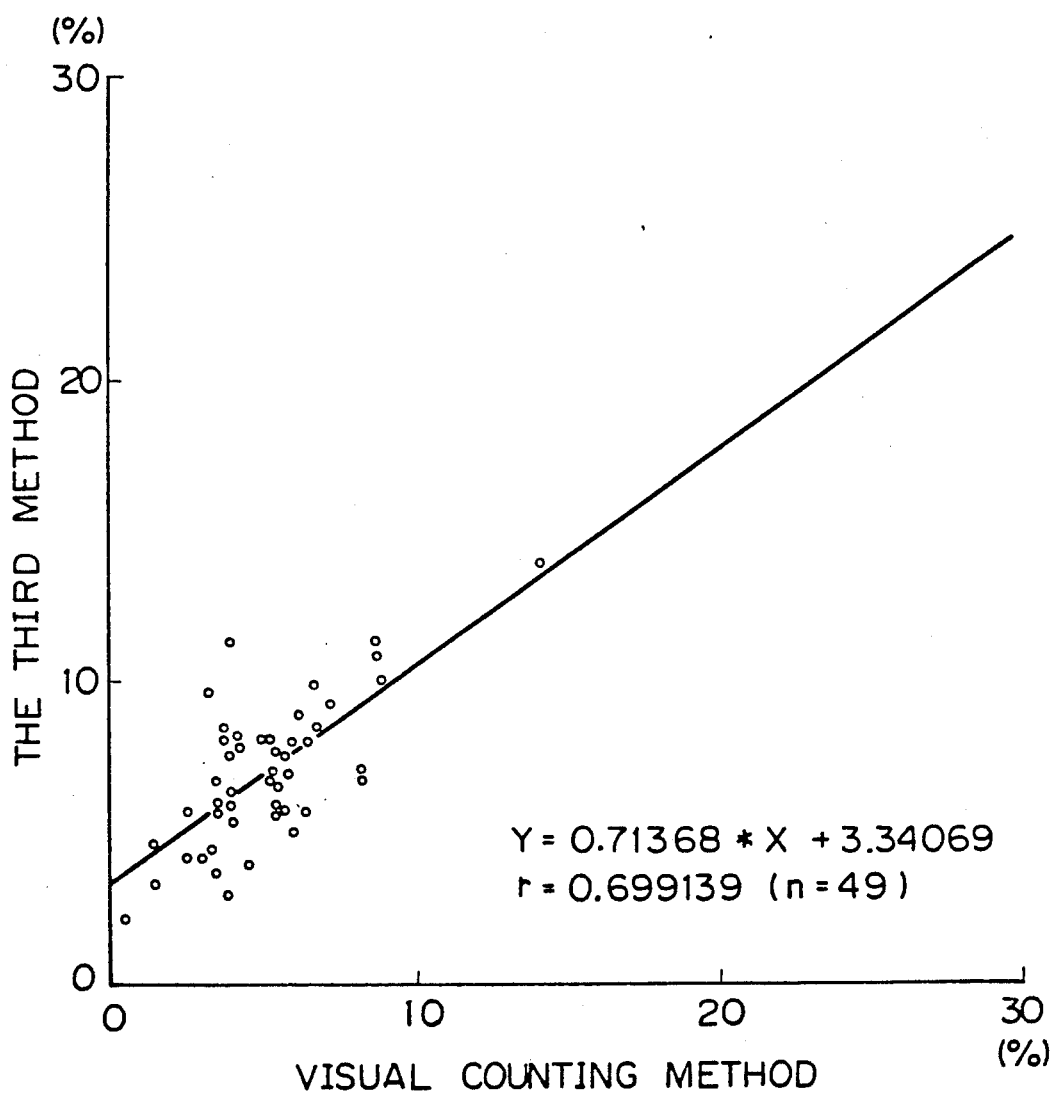
FIGS. 37 to 40 show the results of similar analyses of regression conducted for the percentages of monocytes, neutrophils, eosinophils and basophils, respectively.
Figure 38:
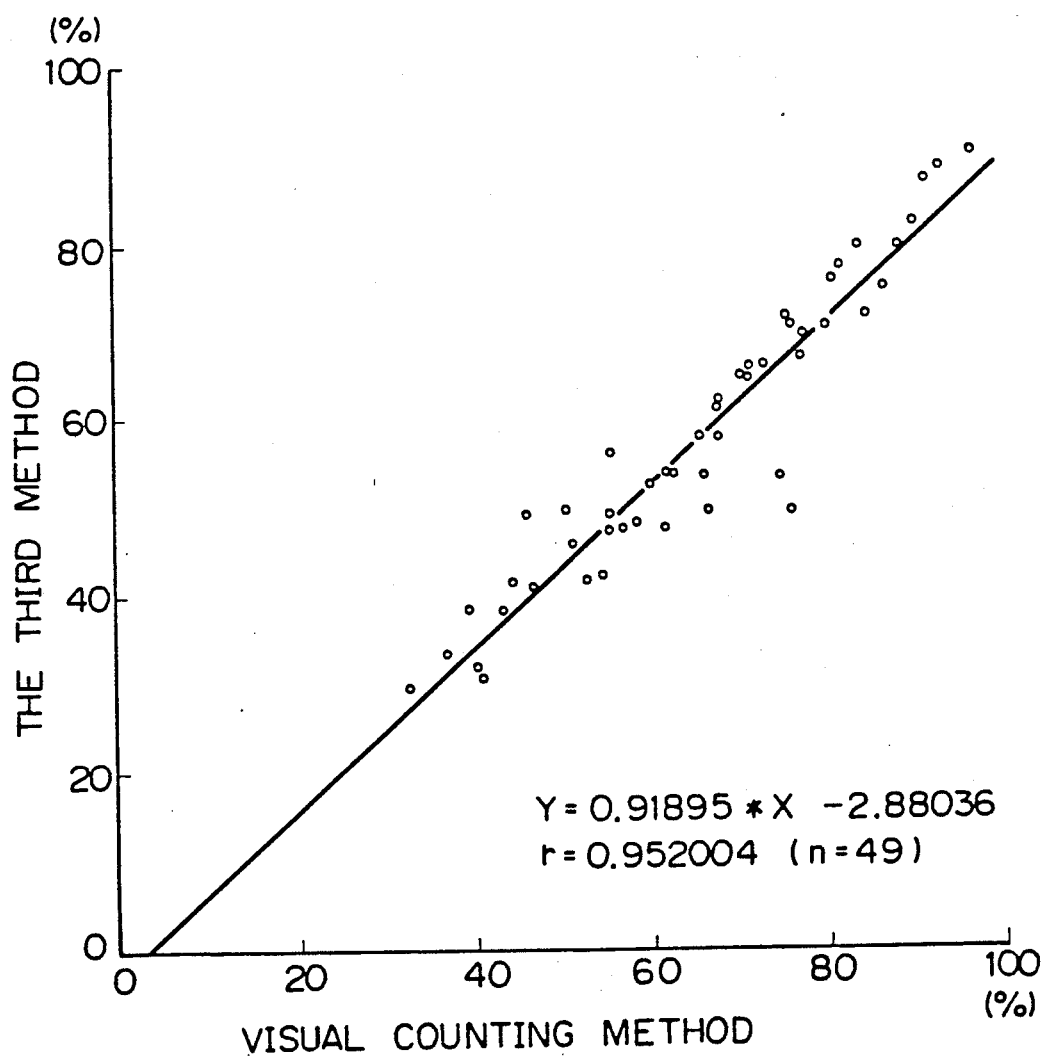
Figure 39:
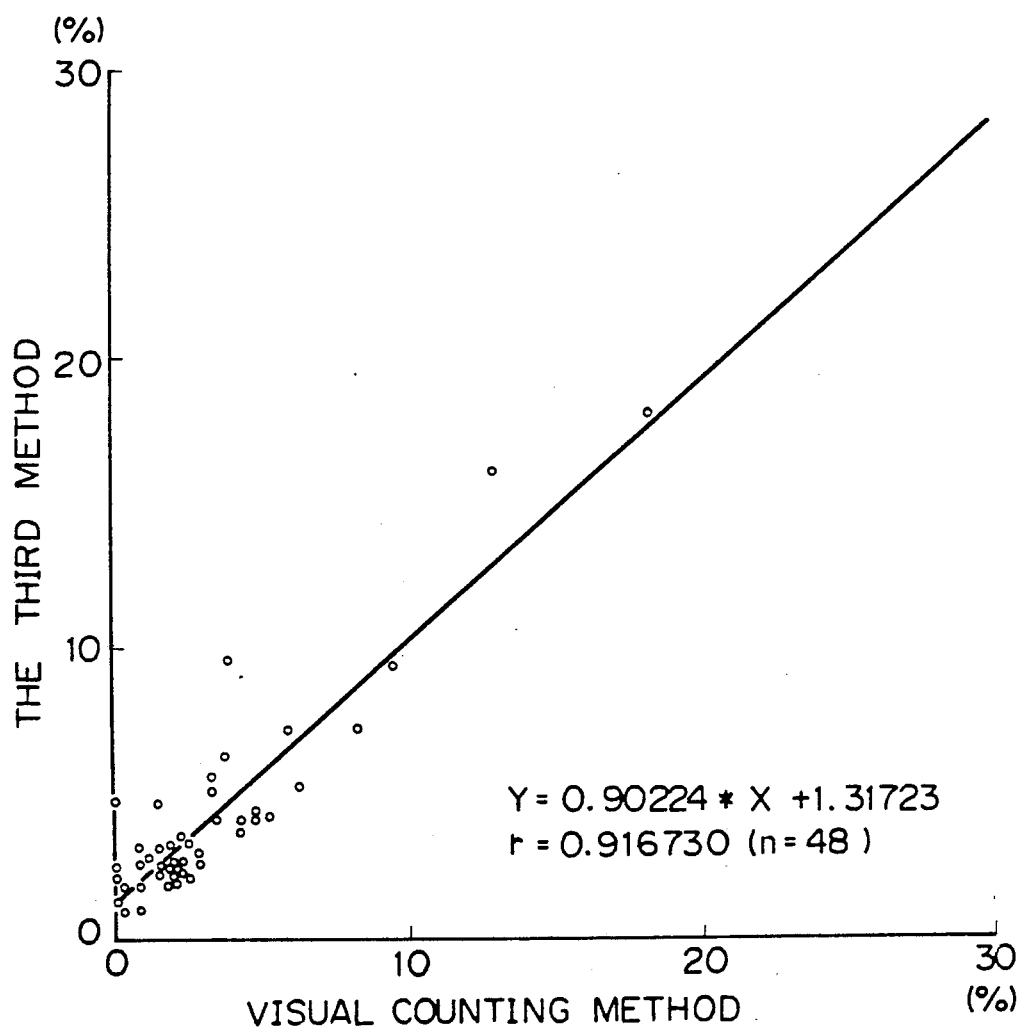
Figure 40:
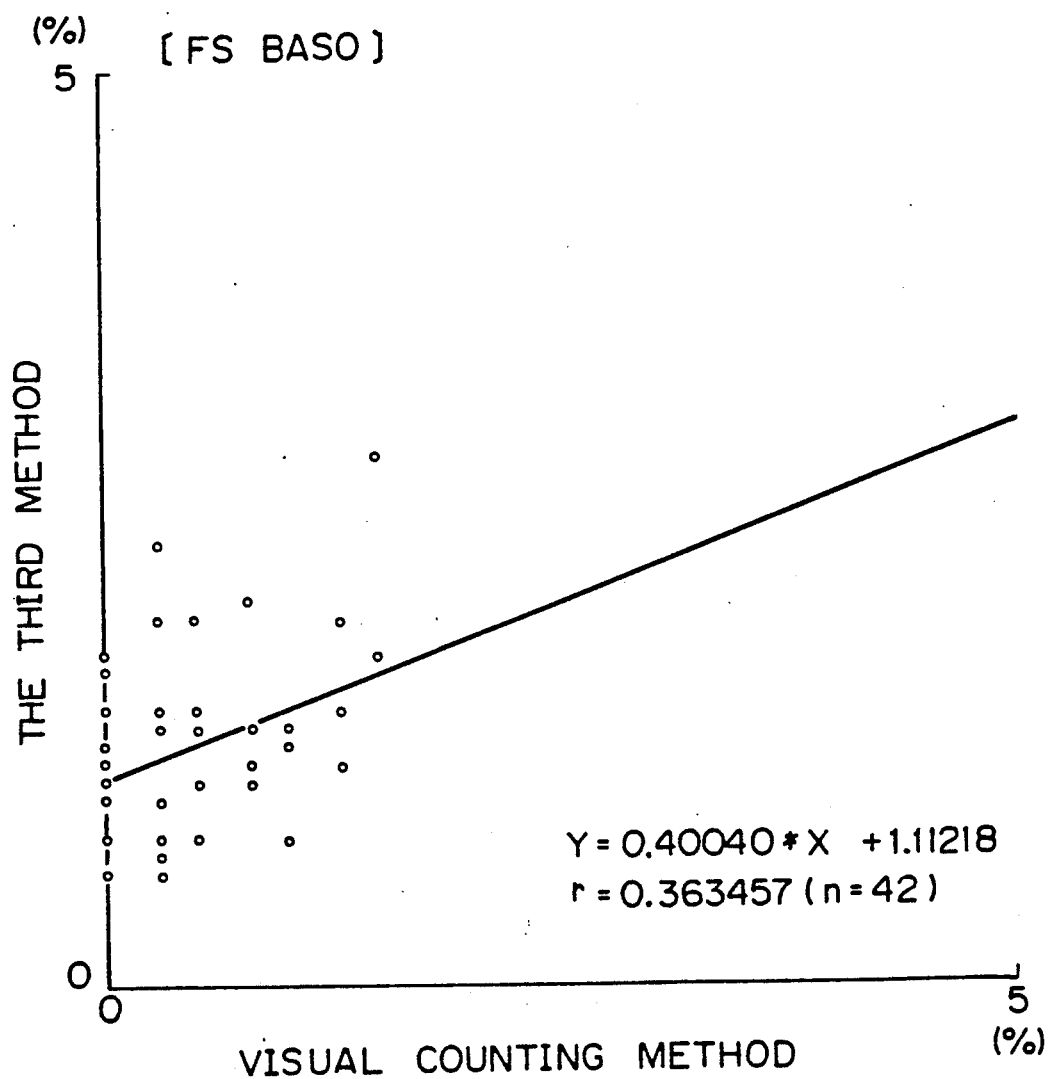

FIG. 36 shows the correlation between the third method of the present invention (i.e., based on measurement of the intensities of forward scattered light and right-angle scattered light) and the visual counting method when each method is applied to measure the percentage of lymphocytes in the leukocytes of interest. The percentage of lymphocytes counted by the visual method is plotted on the X-axis and that counted by the third method of the present invention is plotted on the Y-axis. The straight line in FIG. 36 is the regression line, and the regression of Y upon X is estimated by the equation $Y = 0.94935*X + 3.34446$; r is the correlation coefficient and n is the number of samples. The results of similar analyses of regression conducted for the percentages of monocytes, neutrophils, eosinophils and basophils are graphed in FIGS. 37 to 40, respectively. A good correlation is attained for all leukocyte types except basophils (FIG. 40). Because the absolute number of basophils in blood is small, the accuracy and reproducibility of the data attained by the visual method are inherently low, and this is why there is no good correlation between the visual method and the third method of the present invention.

In Example 3, the erythrocytes in the sample were lysed and fluorescence was used and these contributed to most efficient separation of leukocytes from all other corpuscles. Equally good results can be attained by using a forward scattered light signal. In this latter case, there is no need to use Astrazon Orange R as a dye for staining the nuclei of leukocytes. In addition, a simpler and less costly apparatus will do because it is not necessary to measure the intensity of fluorescence.

In Examples 1 to 3, all measurements are initiated after the necessary procedures of staining or reaction have been completed (namely, after staining or reaction has reached an equilibrium). Therefore, the sample will not experience any time-dependent change during measurements, and an appropriate level of the intensity of staining or reaction can be attained within a certain period of time no matter how large or small the number of leukocytes in the sample is. This allows for consistent results in measurement, and a fluorescence signal of an adequate intensity can be attained even if a light source of a comparatively low output is used. In Examples 1-3 described above, an argon ion laser of 10 mW was employed as a light source in the flow cytometer.

However, the light source in the flow cytometer used in the present invention is not limited to the aforementioned argon ion laser of low output and any of the other light sources can be employed, such as a mercury arc lamp, xenon arc lamp, a He-Cd laser, a He-Ne laser and a Krypton ion laser, as well as an argon ion laser of high output. If these light sources are used, the conditions of staining, reaction and measurement may be selected as appropriate.

The three methods of the present invention as applied to classify and count leukocytes in blood have the following advantages.

(1) A sample for measurement can be prepared by simple preliminary treatments that involve only one step of staining (i.e., addition of anti-coagulated blood to a dye solution) or two-step staining or reaction (i.e., adding a first fluid to anti-coagulated blood, followed by addition of a second fluid).

(2) The sample can be prepared in approximately 1 minute and this provides a rapid access time for measurement.

(3) Since measurements are conducted after the necessary procedures of staining or reaction have been completed, the sample will not experience any time-dependent change during measurements, and an appropriate intensity of staining or reaction can always be attained within a certain period of time irrespective of the nature of the sample (whether it is normal or contains an extremely large or small number of leukocytes). This eliminates the need to change the staining time from sample to sample.

(4) Since measurements are conducted after staining has been completed to provide a high staining intensity, a light source of low output may be employed. In addition, only one light source need be used. In both the one-step and two-step methods, only one channel each of fluorescence and right-angle scattered light signals needs to be measured. In the third method, the parameters to be measured are one channel of forward scattered light and one channel of right-angle scattered light. Because the number of parameters to be measured and analyzed is this few, the present invention can be implemented with a simple and inexpensive apparatus.

(5) In the two-step method and the third method, erythrocytes are selectively lysed by an isotonic treatment under acidic conditions. Since the coincidence of erythrocytes and leukocytes is eliminated by this treatment, a very efficient separation between lymphocytes, monocytes and neutrophils can be achieved by means of a right-angle scattered light signal.

(6) In the one-step and two-step methods, separation of leukocytes from other corpuscles is accomplished by means of the intensity of fluorescence, and in the third method, the same effect is attained by means of the intensity of either fluorescence or forward scattered light. Therefore, correct measurements are ensured in the present invention even if not all erythrocytes have been reduced to fragments.

(7) In accordance with the present invention, the number of dead neutrophilic cells can be counted, so the correct number of neutrophils can be attained even if the blood has been left to stand for a prolonged time after sampling.

(8) The use of a dye (i.e., Astrazon Yellow 3G) that allows for selective staining of both basophils and eosinophils contributes to simplification of the staining procedures.

(9) If fluorescence is not used in the third method for the purpose of separating leukocytes from other corpuscles, the only parameters to be measured are the intensities of forward scattered light and right-angle scattered light. Since the intensity of fluorescence is very small, a photo-multiplier tube of high sensitivity must be employed for its measurement and this adds to the overall cost of the measuring instrument. Right-angle scattered light is more intense than fluorescence and can be measured by a photomultiplier of comparatively low sensitivity. Forward scattered light is so intense that it can be satisfactorily measured with a photodiode. For these reasons, the third method of the present invention can be implemented with an apparatus that is simpler and less costly than the apparatus for the one-step or two-step method.

Whichever method is employed, the present invention ensures accurate and highly reproducible measurements by counting no less than 10,000 leukocytes for each sample.

What is claimed is:

1. An aqueous reagent system for use in the classification of leukocytes into five types by flow cytometry, which comprises a first fluorochrome dye in an amount sufficient for selective staining of eosinophils and basophils, a second fluorochrome dye in an amount sufficient for selective staining of the nuclei of leukocytes, a buffer for maintaining a pH suitable for staining and an osmolarity compensating agent in an amount sufficient for adjusting the osmolarity of the dye solution to a value at which the leukocytes remain unchanged in shape, wherein the first fluorochrome dye is Astrazon Yellow 3G.

2. An aqueous reagent system according to claim 1, wherein the second fluorochrome dye, for staining the nuclei of leukocytes, is at least one member selected from the group consisting of the following dyes:

Acridine Red;
Rhodamine S;
Rhodamine 6G;

Rhodamine B;
Rhodamine 19 perchlorate;
Rhodamine 123;
Eosin Y;
Cyanosine;
Cresyl Fast Violet;
Darrow Red;
Acronol Phloxine FFS;
1,1'-dimethylthiocarbocyanine;
1,1'-diethylthiocarbocyanine;
1,1'-diethyl-9-methylthiocarbocyanine bromide;
[2-[γ-1'-ethyl-4',5'-benzothiazolylidene)propenyl]-1-ethyl-4,5-benzoxazolium iodide];
Astrazon Red 6B;
C.I. Basic Violet 16;
2-(p-dimethylaminostyryl)-1-ethyl-4,5-benzothiazolium iodide;
2,4-bis(p-dimethylaminostyryl)-1-ethyl-pyridinium iodide;
2,6-bis(p-dimethylaminostyryl)-1-ethyl-pyridinium iodide;
Astrazon Orange R.

* * * * *

UNITED STATES PATENT AND TRADEMARK OFFICE
CERTIFICATE OF CORRECTION

PATENT NO.  : 5,039,613
DATED       : August 13, 1991
INVENTOR(S) : Matsuda et al.

It is certified that error appears in the above-identified patent and that said Letters Patent is hereby corrected as shown below:

Title Page:

[56] Other Publications: the last Shapiro citation, after "Geometry?"", insert --25--.

Column 5, line 68, before "Okayama, Japan):" delete "Astrazon Orange R.".
Column 5, line 68, after "and" insert --Astrazon Orange R.--.
Column 15, line 21, delete "Reagents:".
Column 15, line 62, delete "Reagents:".
Column 17, line 52, delete "Reagents:".

Signed and Sealed this

Ninth Day of March, 1993

Attest:

STEPHEN G. KUNIN

Attesting Officer     Acting Commissioner of Patents and Trademarks